US 7,790,160 B2
Sep. 7, 2010

(12) United States Patent
Von Strandmann et al.

(54) METHOD OF TREATING CD30 POSITIVE LYMPHOMAS

(75) Inventors: Elke Pogge Von Strandmann, Cologne (DE); Andreas Engert, Cologne (DE); Peter Borchmann, Cologne (DE); Boris Boell, Cologne (DE)

(73) Assignee: Medarex, Inc., Princeton, NJ (US)

( * ) Notice: Subject to any disclaimer, the term of this patent is extended or adjusted under 35 U.S.C. 154(b) by 121 days.

(21) Appl. No.: 11/241,154

(22) Filed: Sep. 30, 2005

(65) Prior Publication Data

US 2006/0177442 A1  Aug. 10, 2006

Related U.S. Application Data

(60) Provisional application No. 60/615,284, filed on Oct. 1, 2004.

(51) Int. Cl.
*A61K 39/395* (2006.01)

(52) U.S. Cl. .................................. 424/130.1; 530/388.1

(58) Field of Classification Search ........................ None
See application file for complete search history.

(56) References Cited

U.S. PATENT DOCUMENTS

| | | | |
|---|---|---|---|
| 5,165,923 A | 11/1992 | Thorpe et al. | |
| 5,643,759 A | 7/1997 | Pfreundschub et al. | |
| 5,866,372 A | 2/1999 | Stein et al. | |
| 6,033,876 A | 3/2000 | Lemke et al. | |
| 6,143,869 A | 11/2000 | Goodwin et al. | |
| 6,632,927 B2 | 10/2003 | Adair et al. | |
| 7,387,776 B2 | 6/2008 | Keler et al. | |
| 2002/0064527 A1 | 5/2002 | Mohler et al. | |
| 2003/0157108 A1* | 8/2003 | Presta | 424/145.1 |
| 2004/0006215 A1* | 1/2004 | Keler et al. | 530/388.22 |
| 2005/0054055 A1 | 3/2005 | Kucherlapati et al. | |
| 2006/0127392 A1 | 6/2006 | de Romeuf et al. | |

FOREIGN PATENT DOCUMENTS

| | | |
|---|---|---|
| EP | 0657533 A1 | 6/1995 |
| EP | 0613497 B1 | 7/1997 |
| EP | 0805871 B1 | 11/1999 |
| WO | WO-91/07437 A2 | 5/1991 |
| WO | WO-91/07941 A2 | 6/1991 |
| WO | WO-92/03918 A1 | 3/1992 |
| WO | WO-93/10232 A1 | 5/1993 |
| WO | WO-94/04189 A1 | 3/1994 |
| WO | WO-94/25585 A1 | 11/1994 |
| WO | WO-96/22384 A1 | 7/1996 |
| WO | WO-97/17374 A1 | 5/1997 |
| WO | WO-98/24884 | 6/1998 |
| WO | WO-98/24893 A2 | 6/1998 |
| WO | WO-99/40187 A1 | 8/1999 |
| WO | WO-01/11059 A1 | 2/2001 |
| WO | WO-02/11767 A2 | 2/2002 |
| WO | WO-02/17979 A2 | 3/2002 |
| WO | WO-02/43661 A2 | 6/2002 |
| WO | WO-03/059282 A2 | 7/2003 |
| WO | 03/080672 A1 | 10/2003 |
| WO | WO-2004/029092 A2 | 4/2004 |
| WO | WO-2006/039644 A2 | 4/2006 |
| WO | WO-2006/089232 A2 | 8/2006 |

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Coleman P. M., Research in Immunology, 145:33-36, 1994.*
MacCallum et al., J. Mol. Biol., 262, 732-745, 1996.*
Casset et al., Biochemical and Biophysical Research Communications, 307:198-205, 2003.*
O'Connor , Curr Treat Oncol, Aug. 2004, 5:269-281.*
Granziero et al., Eur. J. Immunol. 1999, 29:1127-1138.*
Byers, T. , CA Journal, vol. 49, No. 6, Nov./Dec. 1999.*
Orlowski et al, J Clin Oncol, 2002, 20:4420-4427.*
(http://weisenthal.org/synergy1.htm, Aug. 5, 2008.*
Berenbaum, Synergy, additivism and antagonism in immunosuppression, Clin exp Immunol, 1997, 28:1-18.*
Almond, J.B. et al, "Proteasome inhibitor-induced apoptosis of B-chronic lymphocytic leukaemia cells involves cytochrome c release and caspase activation, accompanied by formation of an ~700 kDa Apaf-1 containing apoptosome complex," *Leukemia*, vol. 15:1388-1397 (2001).
An, J. et al., "Antitumor effects of bortezomib (PS-341) on primary effusion lymphomas," *Leukemia*, vol. 18:1699-1704 (2004).
Böll, Boris et al, "The fully human anti-CD30 antibody 5F11 activates Nf-κB and sensitizes lymphoma cells to bortezomib-induced apoptosis," *Blood*, vol. 106(5):1839-1842 (2005).
Borchmann, Peter et al, "The human anti-CD30 antibody 5F11 shows in vitro and in vivo activity against malignant lymphoma," *Blood*, vol. 102(10):3737-3742 (2003).
Heuck, Friederike et al, "Combination of the Human Anti-CD30 Antibody 5F11 with Cytostatic Drugs Enhances Its Antitumor Activity against Hodgkin and Anaplastic Large Cell Lymphoma Cell Lines," *J. Immunother.*, vol. 27(5):347-353 (2004).
Horie, Ryouichi et al, "Ligand-independent signaling by overexpressed CD30 drives NF-κB activation in Hodgkin-Reed-Sternberg cells," *Oncogene*, Vo. 21:2493-2503 (2002).
Levi, Edi et al, "CD30-activation-mediated growth inhibition of anaplastic large-cell lymphoma cell lines: apoptosis or cell-cycle arrest?" *Blood*, vol. 98(5):1630-1632 (2001).
Mir, Samy S. et al, "Differential effects of CD30 activation in anaplastic large cell lymphoma and Hodgkin disease cells," *Blood*, vol. 96(13):4307-4312 (2000).
Watanabe, Ken-ichiro et al, "Prevention of Etoposide-Induced Apoptosis by Proteaseome Inhibitors in a Human Leukemic Cell Line but Not in Fresh Acute Leukemia Blasts, A Differential Role of NF-κB Activation," *Biochemical Pharmacology*, vol. 60:823-830 (2000).
Yeung, S. Jim et al, "Ubiquitin-Proteasome Pathway Mediates Intracellular Degradation of Apolipoprotein B," *Biochemistry*, vol. 35:13843-13848 (1996).

(Continued)

*Primary Examiner*—Misook Yu
*Assistant Examiner*—Mark Halvorson
(74) *Attorney, Agent, or Firm*—Lahive & Cockfield, LLP; Jane E. Remillard; Jeanne M. DiGiorgio

(57) ABSTRACT

Methods for treating lymphomas characterized by expression of CD30 using anti-CD30 antibodies and proteasome inhibitors in combination are disclosed.

16 Claims, 4 Drawing Sheets

OTHER PUBLICATIONS

Zheng, Bei et al, "Induction of Cell Cycle Arrest and Apoptosis by Proteasome Inhibitor PS-341 in Hodgkin Disease Cell Lines Is Independent of Inhibitor of Nuclear Factor-κB Mutations or Activation of the CD30, CD40, and RANK Receptors," *Clinical Cancer Research*, vol. 10:3207-3215 (2004).

International Search Report for Application No. PCT/US2005/035477, dated May 17, 2006.

Andreesen, R., et al. "Human macrophages can express the Hodgkin's cell-associated antigen Ki-1 (CD30)" *Am. J. Pathol.* Jan. 1989;134(1):187-92.

Andreesen, R., et al. "A Hodgkin cell-specific antigen is expressed on a subset of auto- and alloactivated T (helper) lymphoblasts" *Blood* Jun. 1984; 63(6):1299-302.

Barth, S., et al. "Ki-4(scFv)-ETA', a new recombinant anti-CD30 immunotoxin with highly specific cytotoxic activity against disseminated Hodgkin tumors in SCID mice" *Blood* Jun. 15, 2000;95(12):3909-14.

Borchmann, P., et al. "Phase 1 trial of the novel bispecific molecule H22xKi-4 in patients with refractory Hodgkin lymphoma" *Blood* Nov. 1, 2000;100(9):3101-7.

Bowen, M., et al. "Functional effects of CD30 on a large granular lymphoma cell line, YT. Inhibition of cytotoxicity, regulation of CD28 and IL-2R, and induction of homotypic aggregation" *J Immunol.* Dec. 1, 1993;151(11):5896-906.

Burns, B., et al. "Ki-1-positive non-Hodgkin's lymphomas. An immunophenotypic, ultrastructural, and morphometric study" *Am J Clin Pathol.* Mar. 1990;93(3):327-32.

Carde, P., et al. "Immunoscintigraphy of Hodgkin's disease: In vivo use of radiolabelled monoclonal antibodies derived from Hodgkin cell lines" *Eur J Cancer.* Apr. 1990;26(4):474-9.

Chiarle, R., et al. "CD30 in normal and neoplastic cells" *Clin Immunol.* Feb. 1999;90(2):157-64.

de Bruin, P.C., et al. "CD30 expression in normal and neoplastic lymphoid tissue: biological aspects and clinical implications" *Leukemia* Oct. 1995;9(10):1620-7.

Durkop, H., et al. "Molecular cloning and expression of a new member of the nerve growth factor receptor family that is characteristic for Hodgkin's disease" *Cell* Feb. 7, 1992;68(3):421-7.

Eckert F., et al. "Follicular lymphoid hyperplasia of the skin with high content of Ki-1 positive lymphocytes" *Am J Dermatopathol.* Aug. 1989;11(4):345-52.

Engert, A., et al. "Treatment of advanced Hodgkin's lymphoma: standard and experimental approaches" *Semin Hematol.* Jul. 1999;36(3):282-9.

Engert, A., et al. "Evaluation of ricin A chain-containing Immunotoxins directed against the CD30 antigen as potential reagents for the treatment of Hodgkin's disease" *Cancer Res.* Jan. 1, 1990;50(1):84-8.

Engert, A., et al. "Antitumor effects of ricin A chain immunotoxins prepared from intact antibodies and Fab' fragments on solid human Hodgkin's disease tumors in mice" *Cancer Res.* May 15, 1990;50(10):2929-35.

Falini, B., et al. "In vivo targeting of Hodgkin and Reed-Sternberg cells of Hodgkin's disease with monoclonal antibody Ber-H2 (CD30): immunohistological evidence" *Br J Haematol.* Sep. 1992;82(1):38-45.

Falini, B., et al. "Response of refractory Hodgkin's disease to monoclonal anti-CD30 immunotoxin" *Lancet* May 16, 1992;339(8803):1195-6.

Froese, P., et al. "Biochemical characterization and biosynthesis of the Ki-1 antigen in Hodgkin-derived and virus-transformed human B and T lymphoid cell lines" *J Immunol.* Sep. 15, 1987;139(6):2081-7.

Gruss, H.J. et al. "Pleiotropic effects of the CD30 ligand on CD30-expressing cells and lymphoma cell lines" *Blood* Apr. 15, 1994;83(8):2045-56.

Hecht, T., et al. "Production and characterization of a monoclonal antibody that binds Reed-Sternberg cells" *J Immunol.* Jun. 1985;134(6):4231-6.

Horn-Lohrens, O., et al. "Shedding of the soluble form of CD30 from the Hodgkin-analogous cell line L540 is strongly inhibited by a new CD30-specific antibody (Ki-4)" *Int J Cancer.* Feb. 8, 1995;60(4):539-44.

Hsu, S.M., et al. "Effect of monoclonal antibodies anti-2H9, anti-IRac, and anti-HeFi-1 on the surface antigens of Reed-Sternberg cells" *J Natl Cancer Inst.* Nov. 1987;79(5):1091-9.

Hubinger, G., et al. "CD30-mediated cell cycle arrest associated with induced expression of p21(CIP1/WAF1) in the anaplastic large cell lymphoma cell line Karpas 299" *Oncogene.* Feb. 1, 2001;20(5):590-8.

Josimovic-Alasevic, O., et al. "Ki-1 (CD30) antigen is released by Ki-1-positive tumor cells in vitro and in vivo. I. Partial characterization of soluble Ki-1 antigen and detection of the antigen in cell culture supernatants and in serum by an enzyme-linked immunosorbent assay" *Eur J Immunol.* Jan. 1989;19(1):157-62.

Koon, H., et al. "Anti-CD30 antibody-based therapy" *Curr. Opin. Oncol.* Nov. 2000;12(6):588-93.

May, R. D., et al. "Evaluation of ricin A chain-containing immunotoxins directed against different epitopes on the delta-chain of cell surface-associated IgD on murine B cells" *J Immunol.* May 1, 1990;144(9):3637-42.

Mechtersheimer, G., et al. "Expression of Ki-1 antigen (CD30) in mesenchymal tumors," *Cancer* Oct. 15, 1990;66(8):1732-7.

Miettinen, M., "CD30 distribution. Immunohistochemical study on formaldehyde-fixed, paraffin-embedded Hodgkin's and non-Hodgkin's lymphomas" *Arch Pathol Lab Med.* Nov. 1992;116(11):1197-1201.

Pallesen, G., et al. "The diagnostic significance of the CD30 (Ki-1) antigen" *Histopathology* Apr. 1990;16(4):409-13.

Pallesen, G., et al. "Ki-1 (CD30) antigen is regularly expressed by tumor cells of embryonal carcinoma" *Am J Pathol.* Dec. 1988;133(3):446-50.

Piris, M., et al. "CD30 expression in non-Hodgkin's lymphoma" *Histopathology* Sep. 1990;17(3):211-8.

Pfreundschuh, M., et al. "Hodgkin and Reed-Sternberg cell associated monoclonal antibodies HRS-1 and HRS-2 react with activated cells of lymphoid and monocytoid origin" *Anticancer Res.* Mar.-Apr. 1988;8(2):217-24.

Pohl, C., et al. "CD30-specific AB1-AB2-AB3 internal image antibody network: potential use as anti-idiotype vaccine against Hodgkin's lymphoma" *Int. J. Cancer* May 28, 1993;54(3):418-25.

Press, O.W., et al. "Ricin A-chain containing immunotoxins directed against different epitopes on the CD2 molecule differ in their ability to kill normal and malignant T cells" *J. Immunol.* Dec. 15, 1988;141(12):4410-7.

Schnell, R., et al. "A Phase I study with an anti-CD30 ricin A-chain immunotoxin (Ki-4.dgA) in patients with refractory CD30+ Hodgkin's and non-Hodgkin's lymphoma" *Clin. Cancer Res.* Jun. 2002;8(6):1779-86.

Schwab, U., "Production of a monoclonal antibody specific for Hodgkin and Sternberg-Reed cells of Hodgkin's disease and a subset of normal lymphoid cells" *Nature* Sep. 2, 1982;299(5878):65-7.

Schwarting, R., et al. "BER-H2: a new anti-Ki-1 (CD30) monoclonal antibody directed at a formol-resistant epitope" *Blood* Oct. 1989;74(5):1678-89.

Stein, H., et al. "The expression of the Hodgkin's disease associated antigen Ki-1 in reactive and neoplastic lymphoid tissue: evidence that Reed-Sternberg cells and histiocytic malignancies are derived from activated lymphoid cells" *Blood* Oct. 1985;66(4):848-58.

Tian, Z. G., et al. "In vivo antitumor effects of unconjugated CD30 monoclonal antibodies on human anaplastic large-cell lymphoma xenografts" *Cancer Res.* Nov. 15, 1995:55(22):5335-41.

Tutt, A. L., et al. "Monoclonal antibody therapy of B cell lymphoma: signaling activity on tumor cells appears more important than recruitment of effectors" *J. Immunol.* Sep. 15, 1998;161(6):3176-85.

Tsutsumi, Y., et al. "Site-specific chemical modification with polyethylene glycol of recombinant immunotoxin anti-Tac(Fv)-PE38 (LMB-2) improves antitumor activity and reduces animal toxicity and immunogenicity" *PNAS* 2000 97 (15):8548-8553.

Wahl, A., et al. "The anti-CD30 monoclonal antibody SGN-30 promotes growth arrest and DNA fragmentation in vitro and affects antitumor activity in models of Hodgkin's disease" *Cancer Res.* Jul. 1, 2002;62(13):3736-42.

Clynes, Raphael A. et al., "Inhibitory Fc receptors modulate in vivo cytoxicity against tumor targets," *Nature Medicine*, vol. 6(4):443-446 (2000).

Klimka, A. et al., "Human anti-CD30 recombinant antibodies by guided phage antibody selection using cell panning," *British Journal of Cancer*, vol. 83(2):252-260 (2000).

Lonberg, Nils et al., "Human Antibodies from Transgenic Mice," *Intern. Rev. Immunol.*, vol. 13:65-93 (1995).

Panka, David J. et al., "Variable region framework differences result in decreased or increased affinity of variant anti-digoxin antibodies," *Proc. Natl. Acad. Sci.* USA, vol. 85:3080-3084 (1988).

Shinkawa, Toyohide et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," *The Journal of Biological Chemistry*, vol. 278(5):3466-3473 (2003).

Yamane-Ohnuki, Naoko et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity," *Biotechnology and Bioengineering*, vol. 87(5):614-622 (2004).

Tamura, Midori et al., "Structural Correlates of an Anticarcinoma Antibody: Identification of a Specificity-Determining Residues (SDRs) and Development of a Minimally Immunogenic Antibody Variant by Retention of SDRs Only," The Journal of Immunology, vol. 164:1432-1441 (2000).

International Preliminary Report on Patentability and Written Opinion for Application No. PCT/US2006/005854, dated Aug. 21, 2007.

International Search Report for Application No. PCT/US2006/005854, dated Nov. 2, 2006.

* cited by examiner

SEQUENCE LISTING

<160> NUMBER OF SEQ ID NOS: 53

<210> SEQ ID NO 1
<211> LENGTH: 348
<212> TYPE: DNA
<213> ORGANISM: Homo sapiens
<220> FEATURE:
<221> NAME/KEY: CDS
<222> LOCATION: (1)...(348)

<400> SEQUENCE: 1

```
gag gtg cag ttg gtg gag tct ggg gga ggc ttg gtc cag cct ggg ggg        48
Glu Val Gln Leu Val Glu Ser Gly Gly Gly Leu Val Gln Pro Gly Gly
 1               5                  10                  15 tcc ctg aga ctc tcc tgt gta gcc tct gga ttc acc ttt agt aac tct        96
Ser Leu Arg Leu Ser Cys Val Ala Ser Gly Phe Thr Phe Ser Asn Ser
            20                  25                  30 tgg atg agc tgg gtc cgc cag gct cca ggg aaa ggg ctg gag tgg gtg       144
Trp Met Ser Trp Val Arg Gln Ala Pro Gly Lys Gly Leu Glu Trp Val
        35                  40                  45 gcc aac ata aac gaa gat gga agt gag aaa ttc tat gtg gac tct gtg       192
Ala Asn Ile Asn Glu Asp Gly Ser Glu Lys Phe Tyr Val Asp Ser Val
    50                  55                  60 aag ggc cga ttc acc ttc tcc aga gac aac gcc gag aac tca ctg tat       240
Lys Gly Arg Phe Thr Phe Ser Arg Asp Asn Ala Glu Asn Ser Leu Tyr
 65                 70                  75                  80 ctg caa atg aac agc ctg aga gcc gag gac acg gct gtg tat tac tgt       288
Leu Gln Met Asn Ser Leu Arg Ala Glu Asp Thr Ala Val Tyr Tyr Cys
                85                  90                  95 gcg agg gtt cat tgg tac ttc cat ctc tgg ggc cgt ggc acc ctg gtc       336
Ala Arg Val His Trp Tyr Phe His Leu Trp Gly Arg Gly Thr Leu Val
            100                 105                 110 act gtc tcc tca                                                       348
Thr Val Ser Ser
        115
```

<210> SEQ ID NO 2
<211> LENGTH: 116
<212> TYPE: PRT
<213> ORGANISM: Homo sapiens

<400> SEQUENCE: 2

```
Glu Val Gln Leu Val Glu Ser Gly Gly Gly Leu Val Gln Pro Gly Gly
 1               5                  10                  15

Ser Leu Arg Leu Ser Cys Val Ala Ser Gly Phe Thr Phe Ser Asn Ser
            20                  25                  30

Trp Met Ser Trp Val Arg Gln Ala Pro Gly Lys Gly Leu Glu Trp Val
        35                  40                  45

Ala Asn Ile Asn Glu Asp Gly Ser Glu Lys Phe Tyr Val Asp Ser Val
    50                  55                  60

Lys Gly Arg Phe Thr Phe Ser Arg Asp Asn Ala Glu Asn Ser Leu Tyr
 65                 70                  75                  80

Leu Gln Met Asn Ser Leu Arg Ala Glu Asp Thr Ala Val Tyr Tyr Cys
                85                  90                  95

Ala Arg Val His Trp Tyr Phe His Leu Trp Gly Arg Gly Thr Leu Val
            100                 105                 110

Thr Val Ser Ser
        115
```

```
<210> SEQ ID NO 3
<211> LENGTH: 324
<212> TYPE: DNA
<213> ORGANISM: Homo sapiens
<220> FEATURE:
<221> NAME/KEY: CDS
<222> LOCATION: (1)...(324)

<400> SEQUENCE: 3 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
 1               5                  10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
             20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
         35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
     50                  55                  60 ggc agt ggg tct ggg aca gac ttc act ctc acc atc agc agc ctg gag     240
Gly Ser Gly Ser Gly Thr Asp Phe Thr Leu Thr Ile Ser Ser Leu Glu
 65                  70                  75                  80 cct gaa gat ttt gca gtg tat tac tgt cag cag tat ggt agc tca ccg     288
Pro Glu Asp Phe Ala Val Tyr Tyr Cys Gln Gln Tyr Gly Ser Ser Pro
                 85                  90                  95 tgg acg ttc ggc caa ggg acc aag gtg gaa atc aaa                     324
Trp Thr Phe Gly Gln Gly Thr Lys Val Glu Ile Lys
            100                 105

<210> SEQ ID NO 4
<211> LENGTH: 108
<212> TYPE: PRT
<213> ORGANISM: Homo sapiens

<400> SEQUENCE: 4

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys
            100                 105

<210> SEQ ID NO 5
<211> LENGTH: 348
<212> TYPE: DNA
<213> ORGANISM: Homo sapiens
<220> FEATURE:
<221> NAME/KEY: CDS
<222> LOCATION: (1)...(348)

<400> SEQUENCE: 5
```

```
cag gtg cag cta cag cag tgg ggc gca gga ctg ttg aag cct tcg gag      48
Gln Val Gln Leu Gln Gln Trp Gly Ala Gly Leu Leu Lys Pro Ser Glu
 1               5                  10                  15 acc ctg tcc ctc acc tgc gct gtc tat ggt ggg tcc ttc agt ggt tac      96
Thr Leu Ser Leu Thr Cys Ala Val Tyr Gly Gly Ser Phe Ser Gly Tyr
             20                  25                  30 tac tgg agc tgg atc cgc cag ccc cca ggg aag ggg ctg gag tgg att     144
Tyr Trp Ser Trp Ile Arg Gln Pro Pro Gly Lys Gly Leu Glu Trp Ile
         35                  40                  45 ggg gaa atc aat cat agt gga agc acc aag tac acc ccg tcc ctc aag     192
Gly Glu Ile Asn His Ser Gly Ser Thr Lys Tyr Thr Pro Ser Leu Lys
     50                  55                  60 agc cga gtc acc ata tca gta gac acg tcc aag cac caa ttc tcc ctg     240
Ser Arg Val Thr Ile Ser Val Asp Thr Ser Lys His Gln Phe Ser Leu
 65                  70                  75                  80 aag ctg agc tct gtg acc gcc gcg gac acg gct gtg tat tac tgt gcg     288
Lys Leu Ser Ser Val Thr Ala Ala Asp Thr Ala Val Tyr Tyr Cys Ala
                 85                  90                  95 aga gag act gtc tac tac ttc gat ctc tgg ggc cgt ggc acc ctg gtc     336
Arg Glu Thr Val Tyr Tyr Phe Asp Leu Trp Gly Arg Gly Thr Leu Val
            100                 105                 110 act gtc tcc tca                                                     348
Thr Val Ser Ser
        115

<210> SEQ ID NO 6
<211> LENGTH: 116
<212> TYPE: PRT
<213> ORGANISM: Homo sapiens

<400> SEQUENCE: 6

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45

Gly Glu Ile Asn His Ser Gly Ser Thr Lys Tyr Thr Pro Ser Leu Lys
     50                  55                  60

Ser Arg Val Thr Ile Ser Val Asp Thr Ser Lys His Gln Phe Ser Leu
 65                  70                  75                  80

Lys Leu Ser Ser Val Thr Ala Ala Asp Thr Ala Val Tyr Tyr Cys Ala
                 85                  90                  95

Arg Glu Thr Val Tyr Tyr Phe Asp Leu Trp Gly Arg Gly Thr Leu Val
            100                 105                 110

Thr Val Ser Ser
        115

<210> SEQ ID NO 7
<211> LENGTH: 321
<212> TYPE: DNA
<213> ORGANISM: Homo sapiens
<220> FEATURE:
<221> NAME/KEY: CDS
<222> LOCATION: (1)...(321)

<400> SEQUENCE: 7 gaa att gtg ttg aca cag tct cca gcc acc ctg tct ttg tct cca ggg      48
Glu Ile Val Leu Thr Gln Ser Pro Ala Thr Leu Ser Leu Ser Pro Gly
 1               5                  10                  15
```

| | | |
|---|---|---|
| gaa aga gcc acc ctc tcc tgc agg gcc agt cag agt gta agc agc aac<br>Glu Arg Ala Thr Leu Ser Cys Arg Ala Ser Gln Ser Val Ser Ser Asn<br>20 25 30 | | 96 |
| tta gcc tgg tac caa cag aaa cct ggc cag gct ccc agg ctc ctc atc<br>Leu Ala Trp Tyr Gln Gln Lys Pro Gly Gln Ala Pro Arg Leu Leu Ile<br>35 40 45 | | 144 |
| tat gat gca tcc aac agg gcc act ggc atc cca gcc agg ctc agt ggc<br>Tyr Asp Ala Ser Asn Arg Ala Thr Gly Ile Pro Ala Arg Leu Ser Gly<br>50 55 60 | | 192 |
| agt ggg tct ggg aca gac ttc act ctc acc atc agc agc cta gag cct<br>Ser Gly Ser Gly Thr Asp Phe Thr Leu Thr Ile Ser Ser Leu Glu Pro<br>65 70 75 80 | | 240 |
| gaa gat ttt gca gtt tat tac tgt caa cag cgt agc aac tgg ccg tgg<br>Glu Asp Phe Ala Val Tyr Tyr Cys Gln Gln Arg Ser Asn Trp Pro Trp<br>85 90 95 | | 288 |
| acg ttc ggc caa ggg acc aag gtg gaa atc aaa<br>Thr Phe Gly Gln Gly Thr Lys Val Glu Ile Lys<br>100 105 | | 321 |

<210> SEQ ID NO 8
<211> LENGTH: 107
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Leu Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys
            100                 105

<210> SEQ ID NO 9
<211> LENGTH: 336
<212> TYPE: DNA
<213> ORGANISM: Homo sapiens
<220> FEATURE:
<221> NAME/KEY: CDS
<222> LOCATION: (1)...(336)

<400> SEQUENCE: 9

| | | |
|---|---|---|
| cag gtg cag cta cag cag tgg ggc gca gga ctg ttg aag cct tcg gag<br>Gln Val Gln Leu Gln Gln Trp Gly Ala Gly Leu Leu Lys Pro Ser Glu<br>1               5                  10                  15 | | 48 |
| acc ctg tcc ctc acc tgc gct gtc tat ggt ggg tcc ttc agt gct tac<br>Thr Leu Ser Leu Thr Cys Ala Val Tyr Gly Gly Ser Phe Ser Ala Tyr<br>            20                  25                  30 | | 96 |
| tac tgg agc tgg atc cgc cag ccc cca ggg aag ggg ctg gag tgg att<br>Tyr Trp Ser Trp Ile Arg Gln Pro Pro Gly Lys Gly Leu Glu Trp Ile<br>        35                  40                  45 | | 144 |
| ggg gac atc aat cat ggt gga ggc acc aac tac aac ccg tcc ctc aag<br>Gly Asp Ile Asn His Gly Gly Gly Thr Asn Tyr Asn Pro Ser Leu Lys<br>    50                  55                  60 | | 192 |

```
agt cga gtc acc ata tca gta gac acg tcc aag aac cag ttc tcc ctg      240
Ser Arg Val Thr Ile Ser Val Asp Thr Ser Lys Asn Gln Phe Ser Leu
 65                  70                  75                  80 aag ctg aac tct gta acc gcc gcg gac acg gct gtg tat tac tgt gcg      288
Lys Leu Asn Ser Val Thr Ala Ala Asp Thr Ala Val Tyr Tyr Cys Ala
                 85                  90                  95 agc cta act gcc tac tgg ggc cag gga agc ctg gtc acc gtc tcc tca      336
Ser Leu Thr Ala Tyr Trp Gly Gln Gly Ser Leu Val Thr Val Ser Ser
            100                 105                 110

<210> SEQ ID NO 10
<211> LENGTH: 112
<212> TYPE: PRT
<213> ORGANISM: Homo sapiens

<400> SEQUENCE: 10

Gln Val Gln Leu Gln Gln Trp Gly Ala Gly Leu Leu Lys Pro Ser Glu
 1               5                   10                  15

Thr Leu Ser Leu Thr Cys Ala Val Tyr Gly Gly Ser Phe Ser Ala Tyr
            20                  25                  30

Tyr Trp Ser Trp Ile Arg Gln Pro Pro Gly Lys Gly Leu Glu Trp Ile
        35                  40                  45

Gly Asp Ile Asn His Gly Gly Gly Thr Asn Tyr Asn Pro Ser Leu Lys
    50                  55                  60

Ser Arg Val Thr Ile Ser Val Asp Thr Ser Lys Asn Gln Phe Ser Leu
 65                 70                  75                  80

Lys Leu Asn Ser Val Thr Ala Ala Asp Thr Ala Val Tyr Tyr Cys Ala
                85                  90                  95

Ser Leu Thr Ala Tyr Trp Gly Gln Gly Ser Leu Val Thr Val Ser Ser
            100                 105                 110

<210> SEQ ID NO 11
<211> LENGTH: 321
<212> TYPE: DNA
<213> ORGANISM: Homo sapiens
<220> FEATURE:
<221> NAME/KEY: CDS
<222> LOCATION: (1)...(321)

<400> SEQUENCE: 11 gac atc cag atg acc cag tct cca acc tca ctg tct gca tct gta gga       48
Asp Ile Gln Met Thr Gln Ser Pro Thr Ser Leu Ser Ala Ser Val Gly
 1               5                   10                  15 gac aga gtc acc atc act tgt cgg gcg agt cag ggt att agc agc tgg       96
Asp Arg Val Thr Ile Thr Cys Arg Ala Ser Gln Gly Ile Ser Ser Trp
            20                  25                  30 tta acc tgg tat cag cag aaa cca gag aaa gcc cct aag tcc ctg atc      144
Leu Thr Trp Tyr Gln Gln Lys Pro Glu Lys Ala Pro Lys Ser Leu Ile
        35                  40                  45 tat gct gca tcc agt ttg caa agt ggg gtc cca tca agg ttc agc ggc      192
Tyr Ala Ala Ser Ser Leu Gln Ser Gly Val Pro Ser Arg Phe Ser Gly
    50                  55                  60 agt gga tct ggg aca gat ttc act ctc acc atc agc agc ctg cag cct      240
Ser Gly Ser Gly Thr Asp Phe Thr Leu Thr Ile Ser Ser Leu Gln Pro
 65                 70                  75                  80 gaa gat ttt gca act tat tac tgc caa cag tat gat agt tac cct atc      288
Glu Asp Phe Ala Thr Tyr Tyr Cys Gln Gln Tyr Asp Ser Tyr Pro Ile
                85                  90                  95 acc ttc ggc caa ggg aca cga ctg gag att aaa                          321
Thr Phe Gly Gln Gly Thr Arg Leu Glu Ile Lys
            100                 105
```

<210> SEQ ID NO 12
<211> LENGTH: 107
<212> TYPE: PRT
<213> ORGANISM: Homo sapiens

<400> SEQUENCE: 12

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Thr Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Tyr Pro Ile
                85                  90                  95

Thr Phe Gly Gln Gly Thr Arg Leu Glu Ile Lys
            100                 105

<210> SEQ ID NO 13
<211> LENGTH: 15
<212> TYPE: DNA
<213> ORGANISM: Homo sapiens

<400> SEQUENCE: 13
aactcttgga tgagc                                                            15

<210> SEQ ID NO 14
<211> LENGTH: 5
<212> TYPE: PRT
<213> ORGANISM: Homo sapiens

<400> SEQUENCE: 14

Asn Ser Trp Met Ser
1               5

<210> SEQ ID NO 15
<211> LENGTH: 51
<212> TYPE: DNA
<213> ORGANISM: Homo sapiens

<400> SEQUENCE: 15
aacataaacg aagatggaag tgagaaattc tatgtggact ctgtgaaggg c                    51

<210> SEQ ID NO 16
<211> LENGTH: 17
<212> TYPE: PRT
<213> ORGANISM: Homo sapiens

<400> SEQUENCE: 16

Asn Ile Asn Glu Asp Gly Ser Glu Lys Phe Tyr Val Asp Ser Val Lys
1               5                   10                  15

Gly

<210> SEQ ID NO 17
<211> LENGTH: 21
<212> TYPE: DNA

<213> ORGANISM: Homo sapiens

<400> SEQUENCE: 17
gttcattggt acttccatct c					21

<210> SEQ ID NO 18
<211> LENGTH: 5
<212> TYPE: DNA
<213> ORGANISM: Homo sapiens

<400> SEQUENCE: 18 vhwyh					5

<210> SEQ ID NO 19
<211> LENGTH: 36
<212> TYPE: DNA
<213> ORGANISM: Homo sapiens

<400> SEQUENCE: 19
agggccagtc agagtgttag cagcagctac ttagcc					36

<210> SEQ ID NO 20
<211> LENGTH: 12
<212> TYPE: PRT
<213> ORGANISM: Homo sapiens

<400> SEQUENCE: 20

Arg Ala Ser Gln Ser Val Ser Ser Ser Tyr Leu Ala
 1               5                  10

<210> SEQ ID NO 21
<211> LENGTH: 21
<212> TYPE: DNA
<213> ORGANISM: Homo sapiens

<400> SEQUENCE: 21
ggtgcatcca gcagggccac t					21

<210> SEQ ID NO 22
<211> LENGTH: 7
<212> TYPE: PRT
<213> ORGANISM: Homo sapiens

<400> SEQUENCE: 22

Gly Ala Ser Ser Arg Ala Thr
 1               5

<210> SEQ ID NO 23
<211> LENGTH: 27
<212> TYPE: DNA
<213> ORGANISM: Homo sapiens

<400> SEQUENCE: 23
cagcagtatg gtagctcacc gtggacg					27

<210> SEQ ID NO 24
<211> LENGTH: 9
<212> TYPE: PRT
<213> ORGANISM: Homo sapiens

<400> SEQUENCE: 24

Gln Gln Tyr Gly Ser Ser Pro Trp Thr
 1               5

<210> SEQ ID NO 25
<211> LENGTH: 15
<212> TYPE: DNA
<213> ORGANISM: Homo sapiens

<400> SEQUENCE: 25
ggttactact ggagc                                                    15

<210> SEQ ID NO 26
<211> LENGTH: 5
<212> TYPE: PRT
<213> ORGANISM: Homo sapiens

<400> SEQUENCE: 26

Gly Tyr Tyr Trp Ser
 1               5

<210> SEQ ID NO 27
<211> LENGTH: 48
<212> TYPE: DNA
<213> ORGANISM: Homo sapiens

<400> SEQUENCE: 27
gaaatcaatc atagtggaag caccaagtac accccgtccc tcaagagc                48

<210> SEQ ID NO 28
<211> LENGTH: 16
<212> TYPE: PRT
<213> ORGANISM: Homo sapiens

<400> SEQUENCE: 28

Glu Ile Asn His Ser Gly Ser Thr Lys Tyr Thr Pro Ser Leu Lys Ser
 1               5                  10                  15

<210> SEQ ID NO 29
<211> LENGTH: 24
<212> TYPE: DNA
<213> ORGANISM: Homo sapiens

<400> SEQUENCE: 29
gagactgtct actacttcga tctc                                          24

<210> SEQ ID NO 30
<211> LENGTH: 8
<212> TYPE: PRT
<213> ORGANISM: Homo sapiens

<400> SEQUENCE: 30

Glu Thr Val Tyr Tyr Phe Asp Leu
 1               5

<210> SEQ ID NO 31
<211> LENGTH: 33
<212> TYPE: DNA
<213> ORGANISM: Homo sapiens

<400> SEQUENCE: 31
agggccagtc agagtgtaag cagcaactta gcc                                33

<210> SEQ ID NO 32
<211> LENGTH: 11
<212> TYPE: PRT
<213> ORGANISM: Homo sapiens

<400> SEQUENCE: 32

Arg Ala Ser Gln Ser Val Ser Ser Asn Leu Ala
 1               5                  10

<210> SEQ ID NO 33
<211> LENGTH: 21
<212> TYPE: DNA
<213> ORGANISM: Homo sapiens

<400> SEQUENCE: 33
gatgcatcca acagggccac t                                    21

<210> SEQ ID NO 34
<211> LENGTH: 7
<212> TYPE: PRT
<213> ORGANISM: Homo sapiens

<400> SEQUENCE: 34

Asp Ala Ser Asn Arg Ala Thr
 1               5

<210> SEQ ID NO 35
<211> LENGTH: 27
<212> TYPE: DNA
<213> ORGANISM: Homo sapiens

<400> SEQUENCE: 35
caacagcgta gcaactggcc gtggacg                              27

<210> SEQ ID NO 36
<211> LENGTH: 9
<212> TYPE: PRT
<213> ORGANISM: Homo sapiens

<400> SEQUENCE: 36

Gln Gln Arg Ser Asn Trp Pro Trp Thr
 1               5

<210> SEQ ID NO 37
<211> LENGTH: 15
<212> TYPE: DNA
<213> ORGANISM: Homo sapiens

<400> SEQUENCE: 37
gcttactact ggagc                                           15

<210> SEQ ID NO 38
<211> LENGTH: 5
<212> TYPE: PRT
<213> ORGANISM: Homo sapiens

<400> SEQUENCE: 38

Ala Tyr Tyr Trp Ser
 1               5

<210> SEQ ID NO 39
<211> LENGTH: 48
<212> TYPE: DNA
<213> ORGANISM: Homo sapiens

<400> SEQUENCE: 39
gacatcaatc atggtggagg caccaactac aacccgtccc tcaagagt       48

```
<210> SEQ ID NO 40
<211> LENGTH: 16
<212> TYPE: PRT
<213> ORGANISM: Homo sapiens

<400> SEQUENCE: 40

Asp Ile Asn His Gly Gly Gly Thr Asn Tyr Asn Pro Ser Leu Lys Ser
 1               5                  10                  15

<210> SEQ ID NO 41
<211> LENGTH: 12
<212> TYPE: DNA
<213> ORGANISM: Homo sapiens

<400> SEQUENCE: 41
ctaactgcct ac                                                              12

<210> SEQ ID NO 42
<211> LENGTH: 4
<212> TYPE: PRT
<213> ORGANISM: Homo sapiens

<400> SEQUENCE: 42

Leu Thr Ala Tyr
 1

<210> SEQ ID NO 43
<211> LENGTH: 33
<212> TYPE: DNA
<213> ORGANISM: Homo sapiens

<400> SEQUENCE: 43
cgggcgagtc agggtattag cagctggtta acc                                        33

<210> SEQ ID NO 44
<211> LENGTH: 11
<212> TYPE: PRT
<213> ORGANISM: Homo sapiens

<400> SEQUENCE: 44

Arg Ala Ser Gln Gly Ile Ser Ser Trp Leu Thr
 1               5                  10

<210> SEQ ID NO 45
<211> LENGTH: 21
<212> TYPE: DNA
<213> ORGANISM: Homo sapiens

<400> SEQUENCE: 45
gctgcatcca gtttgcaaag t                                                    21

<210> SEQ ID NO 46
<211> LENGTH: 7
<212> TYPE: PRT
<213> ORGANISM: Homo sapiens

<400> SEQUENCE: 46

Ala Ala Ser Ser Leu Gln Ser
 1               5

<210> SEQ ID NO 47
<211> LENGTH: 27
<212> TYPE: DNA
<213> ORGANISM: Homo sapiens
```

```
<400> SEQUENCE: 47
caacagtatg atagttaccc tatcacc                                            27

<210> SEQ ID NO 48
<211> LENGTH: 9
<212> TYPE: PRT
<213> ORGANISM: Homo sapiens

<400> SEQUENCE: 48

Gln Gln Tyr Asp Ser Tyr Pro Ile Thr
  1               5

<210> SEQ ID NO 49
<211> LENGTH: 291
<212> TYPE: DNA
<213> ORGANISM: Homo sapiens

<400> SEQUENCE: 49
caggtgcagc tacagcagtg gggcgcagga ctgttgaagc cttcggagac cctgtccctc        60
acctgcgctg tctatggtgg gtccttcagt ggttactact ggagctggat ccgccagccc       120
ccagggaagg ggctggagtg gattggggaa atcaatcata gtggaagcac caactacaac       180
ccgtccctca agagtcgagt caccatatca gtagacacgt ccaagaacca gttctccctg       240
aagctgagct ctgtgaccgc cgcggacacg gctgtgtatt actgtgcgag a                291

<210> SEQ ID NO 50
<211> LENGTH: 285
<212> TYPE: DNA
<213> ORGANISM: Homo sapiens

<400> SEQUENCE: 50
gacatccaga tgacccagtc tccatcctca ctgtctgcat ctgtaggaga cagagtcacc        60
atcacttgtc gggcgagtca gggtattagc agctggttag cctggtatca gcagaaacca       120
gagaaagccc ctaagtccct gatctatgct gcatccagtt tgcaaagtgg ggtcccatca       180
aggttcagcg gcagtggatc tgggacagat ttcactctca ccatcagcag cctgcagcct       240
gaagattttg caacttatta ctgccaacag tataatagtt acccct                      285

<210> SEQ ID NO 51
<211> LENGTH: 294
<212> TYPE: DNA
<213> ORGANISM: Homo sapiens

<400> SEQUENCE: 51
gaggtgcagc tggtggagtc tgggggaggc ttggtccagc ctgggggtc cctgagactc         60 tcctgtgcag cctctggatt cacctttagt agctattgga tgagctgggt ccgccaggct       120
ccagggaaag ggctggagtg ggtggccaac ataaagcaag atggaagtga aaatactat        180 gtggactctg tgaagggccg attcaccatc tccagagaca acgccaagaa ctcactgtat       240
ctgcaaatga acagcctgag agccgaggac acggctgtgt attactgtgc gaga             294

<210> SEQ ID NO 52
<211> LENGTH: 288
<212> TYPE: DNA
<213> ORGANISM: Homo sapiens

<400> SEQUENCE: 52
gaaattgtgt tgacgcagtc tccaggcacc ctgtctttgt ctccagggga aagagccacc        60
```

```
ctctcctgca gggccagtca gagtgttagc agcagctact tagcctggta ccagcagaaa      120
cctggccagg ctcccaggct cctcatctat ggtgcatcca gcagggccac tggcatccca      180
gacaggttca gtggcagtgg gtctgggaca gacttcactc tcaccatcag cagactggag      240
cctgaagatt ttgcagtgta ttactgtcag cagtatggta gctcacct                   288

<210> SEQ ID NO 53
<211> LENGTH: 285
<212> TYPE: DNA
<213> ORGANISM: Homo sapiens

<400> SEQUENCE: 53
gaaattgtgt tgacacagtc tccagccacc ctgtctttgt ctccagggga aagagccacc       60
ctctcctgca gggccagtca gagtgttagc agctacttag cctggtacca acagaaacct      120
ggccaggctc ccaggctcct catctatgat gcatccaaca gggccactgg catcccagcc      180
aggttcagtg gcagtgggtc tgggacagac ttcactctca ccatcagcag cctagagcct      240
gaagattttg cagtttatta ctgtcagcag cgtagcaact ggcct                      285
```

METHOD OF TREATING CD30 POSITIVE LYMPHOMAS

RELATED APPLICATIONS

This application claims priority to U.S. Ser. No. 60/615,284, filed on Oct. 1, 2004, the contents of which are incorporated herein by reference.

BACKGROUND OF THE INVENTION

The CD30 cell surface molecule is a member of the tumor necrosis factor receptor (TNF-R) superfamily. This family of molecules has variable homology among its members and includes nerve growth factor receptor (NGFR), CD120(a), CD120(b), CD27, CD40, CD95, OX40, Fas, TNF-R1, and TNF-R2, which are key regulatory molecules that transduce signals from the environment into the cell modulating immune responses (1, 2) These molecules are typically characterized by the presence of multiple cysteine-rich repeats in the extracytoplasmic region (de Bruin, P. C., et al. *Leukemia* 9:1620-1627 (1995)). Members of this family are considered crucial for regulating proliferation and differentiation of lymphocytes.

CD30 is a type I transmembrane glycoprotein with six (human) or three (murine and rat) cysteine-rich repeats with a central hinge sequence. CD30 exists as a 120 kDa membrane molecule which develops from an intercellular precursor protein of 90 kDa. It is shed from the cell surface as a soluble protein (sCD30) of approximately 90 kDa. Shedding of sCD30 occurs as an active process of viable CD30 cells and is not merely caused by the release from dying or dead cells. cDNAs encoding the CD30 protein have been cloned from expression libraries of the HLTV-1 human T-cell line HUT-102 by immunoscreening with monoclonal antibodies Ki-1 and Ber-H2 (Schwab, U., et al. *Nature* 299:65 (1982)). The mouse and rat CD30 cDNA has been found to encode 498 and 493 amino acids, respectively. Human CD30 cDNA encodes an additional 90 amino acids, partially duplicated from one of the cysteine rich domains. The CD30 gene has been mapped to 1p36 in humans and 5q36.2 in rats.

CD30 is preferentially expressed by activated lymphoid cells. The cell surface receptor was originally identified by the monoclonal antibody Ki-1, which is reactive with antigens expressed on Hodgkin and Reed-Sternberg cells of Hodgkin's disease (Schwab et al., *Nature* 299:65 (1982)). Accordingly, CD30 is widely used as a clinical marker for Hodgkin's lymphoma and related hematological malignancies (Froese et al., *J. Immunol.* 139:2081 (1987); Carde et al., *Eur. J. Cancer* 26:474 (1990)). It was later determined that stimulation of CD30 in lymphoid cells has been shown to induce pleiotropic biological effects, including proliferation, activation, differentiation and cell death, depending on cell type, stage of differentiation and presence of other stimuli (Gruss, H. J. et al., *Blood* 83:2045-2056 (1994)). It is believed that the overexpression of CD30 receptor on the malignant cells contributes to survival and apoptosis resistance due to the activation of NF-kB in HD-derived cells (3-5).

CD30 has been shown to be expressed on a subset of non-Hodgkin's lymphomas (NHL), including Burkitt's lymphoma, anaplastic large-cell lymphomas (ALCL), cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), and entroblastic/centrocytic (cb/cc) follicular lymphomas (Stein et al., *Blood* 66:848 (1985); Miettinen, *Arch. Pathol. Lab. Med.* 116:1197 (1992); Piris et al., *Histopathology* 17:211 (1990); Burns et al., *Am. J. Clin. Pathol.* 93:327(1990); and Eckert et al., *Am. J. Dermatopathol.* 11:345 (1989)), as well as several virally-transformed lines such as human T-Cell Lymphotrophic Virus I or II transformed T-cells, and Epstein-Barr Virus transformed B-cells (Stein et al., *Blood* 66:848 (1985); Andreesen et al., *Blood* 63:1299 (1984)). In addition, CD30 expression has been documented in embryonal carcinomas, nonembryonal carcinomas, malignant melanomas, mesenchymal tumors, and myeloid cell lines and macrophages at late stages of differentiation (Schwarting et al., Blood 74:1678 (1989); Pallesen et al., Am J. Pathol. 133:446 (1988); Mechtersheimer et al., Cancer 66:1732 (1990); Andreesen et al., Am. J. Pathol. 134:187 (1989)).

Approximately 20 to 30% of HD patients having advanced age or HD stage will relapse after first line therapy. Of these patients, salvage therapy consisting of high dose drug therapy combined with autologous stem cell transplant can cure an additional 40-60%. Numerous single agent regimens, e.g., oral etoposide, chlorambucil, vinblastine, gemcitabine, vinorelbine, can palliate patients who fail transplant or are ineligible for transplant for months or years (Devizzi et al., Annals of Oncology 5: 817-820, 1994). More recently developed salvage therapies, such as proteasome inhibitors, anti-CD30 antibodies, and combination regimens, e.g., doxil, navelbine and gemcitabine, remain largely ineffective against treating CD30 positive lymphomas with few exceptions.

Since the percentage of CD30-positive cells in normal individuals is quite small, the expression of CD30 in tumor cells renders it an important target for antibody mediated therapy to specifically target therapeutic agents against CD30-positive neoplastic cells (Chaiarle, R., et al. *Clin. Immunol.* 90(2):157-164 (1999)). However, while the results obtained to date clearly establish CD30 as a useful target for immunotherapy, they also show that currently available murine and chimeric antibodies do not constitute ideal therapeutic agents. The fully human anti-CD30 monoclonal antibody 5F11 has been shown effective against ALCL and various HD-derived cell lines in vitro and in vivo (17). Despite the improved efficacy of the fully human antibody over murine and chimeric anti-CD30 antibodies, variations in the sensitivity of CD30 positive target cells to 5F11 have been observed. Improvements in the ability of antibody therapies to kill CD30-expressing cells responsible for CD30 positive lymphomas would be desirable.

Accordingly, there is a need for improved therapeutic antibodies against CD30 which are effective at treating and/or preventing diseases mediated by CD30.

SUMMARY OF THE INVENTION

In the present invention, the effects of 5F11 on NF-kB activation were studied in a variety of HD-derived cell lines to investigate the mechanism of apoptosis resistance. The invention demonstrates improved efficacy of 5F11 in combination with bortezomib, a proteasome inhibitor known to suppress NF-kB activation, both in vitro and in a subcutaneous human Hodgkin tumor model.

Accordingly, the present invention provides methods of treating patients having CD30 positive lymphomas by administering a therapeutically effective amount of an anti-CD30 monoclonal antibody in combination with an inhibitor of NF-kB activity, such as a proteasome inhibitor.

In one embodiment, the anti-CD30 antibody is administered simultaneously with, or at least within 1 day of, the proteasome inhibitor in dosages of antibody ranging from 1 mg/kg to 25 mg/kg and dosages of the proteasome inhibitor ranging from 0.1 mg/kg to 10 mg/kg.

In another embodiment, the anti-CD30 antibody is administered at least 1 day prior to administration of the proteasome inhibitor in dosages of antibody ranging from 1 mg/kg to 25 mg/kg and dosages of the proteasome inhibitor ranging from 0.1 mg/kg to 10 mg/kg.

In yet another embodiment, the anti-CD30 antibody is administered at least 1 week prior to administration of the proteasome inhibitor. Another aspect of this embodiment entails administering the anti-CD30 antibody at least once each week up to 12 weeks prior to administration of the proteasome inhibitor in dosages of antibody ranging from 1 mg/kg to 25 mg/kg and dosages of the proteasome inhibitor ranging from 0.1 mg/kg to 10 mg/kg.

In another embodiment, the anti-CD30 antibody is administered in a single large dose, e.g., 10 to 25 mg/kg, followed by administration of the proteasome inhibitor at least once up to 1 week after antibody administration; least once up to 2 weeks after antibody administration; at least once up to 3 weeks after antibody administration; at least once up to 4 weeks after antibody administration; at least once up to 1 month after antibody administration; at least once up to 2 months after antibody administration; or at least once up to 3 months after antibody administration.

Other features and advantages of the instant invention be apparent from the following detailed description and examples which should not be construed as limiting. The contents of all references, patents and published patent applications cited throughout this application are expressly incorporated herein by reference

DETAILED DESCRIPTION OF THE INVENTION

Figure 1:
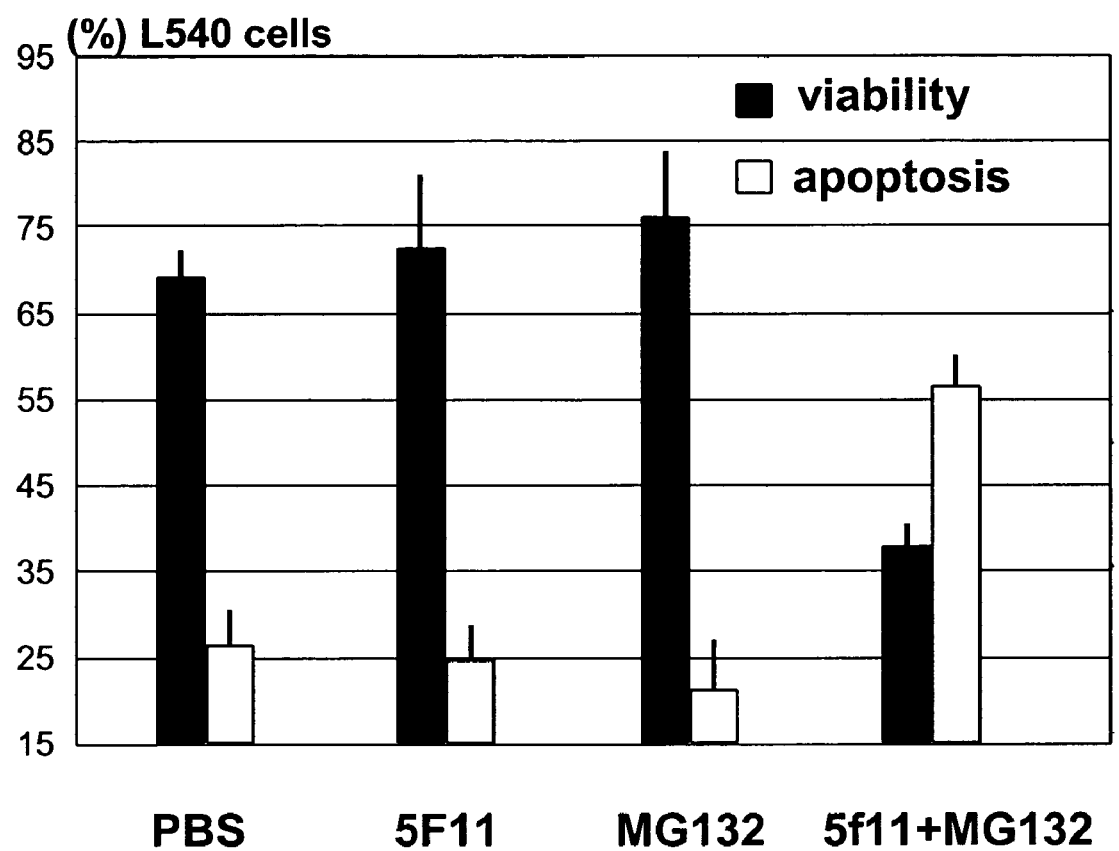
FIG. 1: Induction of apoptosis in L540 cells after treatment with 5F11 and MG132 L540 cells were cultured for 16 h with PBS (control), crosslinked 5F11, MG132 or a combination of 5F11 and MG132. The apoptotic cells were labeled by annexinV-FITC staining and the percentage of viable and apoptotic cells is given as estimated in FACS analysis. The results of three independent experiments are shown.

In order that the present invention may be more readily understood, certain terms are first defined. Additional definitions are set forth throughout the detailed description.

The terms "CD30" and "CD30 antigen" are used interchangeably herein, and include any variants, isoforms and species homologs of human CD30 which are naturally expressed by cells. In a preferred embodiment, binding of an antibody of the invention to the CD30-antigen inhibits the growth of cells expressing CD30 (e.g., a tumor cell) by inhibiting or blocking binding of CD30 ligand to CD30. The term "CD30 ligand" encompasses all (e.g., physiological) ligands for CD30. In a preferred embodiment, the CD30 ligand is CD30L, CD153, TRAF1, TRAF2, TRAF3 or TRAF5. In another preferred embodiment, binding of an antibody of the invention to the CD30-antigen mediates effector cell phagocytosis and/or killing of cells expressing CD30. In yet another preferred embodiment, binding of an antibody of the invention to the CD30-antigen mediates effector cell ADCC of cells expressing CD30.

As used herein, the term "inhibits growth" (e.g., referring to cells) is intended to include any measurable decrease in the growth of a cell when contacted with an anti-CD30 antibody as compared to the growth of the same cell not in contact with an anti-CD30 antibody, e.g., the inhibition of growth of a cell by at least about 10%, 20%, 30%, 40%, 50%, 60%, 70%, 80%, 90%, 99%, or 100%.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

An "isolated antibody", as used herein, is intended to refer to an antibody that is substantially free of other antibodies having different antigenic specificities (e.g., an isolated antibody that specifically binds CD30 is substantially free of antibodies that specifically bind antigens other than CD30). An isolated antibody that specifically binds CD30 may, however, have cross-reactivity to other antigens, such as CD30 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody. The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human Cd30" is intended to refer to an antibody that binds to human CD30 with a $K_D$ of $1 \times 10^{-7}$ M or less, more preferably $5 \times 10^{-8}$ M or less, more preferably $3 \times 10^{-8}$ M or less, more preferably $1 \times 10^{-8}$ M or less, even more preferably $1 \times 10^{-9}$ M or less.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $10^{-8}$ M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$ M or less, even more preferably $10^{-9}$ M or less.

As used herein, the terms "subject" and "patient" are used interchangeably and can refer to any human or nonhuman animal. The term "nonhuman animal" includes all vertebrates, e.g., mammals and non-mammals, such as nonhuman primates, sheep, dogs, cats, horses, cows, chickens, amphibians, reptiles, etc. In a particular embodiment of the present invention the patient is a human.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., CD30). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

As used herein, the terms "inhibits binding" and "blocks binding" (e.g., referring to inhibition/blocking of binding of CD30 ligand to CD30. Inhibition/blocking are used interchangeably and encompass both partial and complete inhibition/blocking. The inhibition/blocking of CD30 preferably reduces or alters the normal level or type of activity that occurs when CD30 binding occurs without inhibition or blocking, e.g., inhibition of CD30 induced proliferation. Inhibition and blocking are also intended to include any measurable decrease in the binding affinity of CD30 when in contact with an anti-CD30 antibody as compared to CD30 not in contact with an anti-CD30 antibody, e.g., the blocking of CD30 to its receptor by at least about 10%, 20%, 30%, 40%, 50%, 60%, 70%, 80%, 90%, 99% or 100%.

The term "bispecific molecule" is intended to include any agent, e.g., a protein, peptide, or protein or peptide complex, which has two different binding specificities. For example, the molecule may bind to, or interact with, (a) a cell surface antigen and (b) an Fc receptor on the surface of an effector cell. The term "multispecific molecule" or "heterospecific molecule" is intended to include any agent, e.g., a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to cell surface antigens, such as CD30, and to other targets, such as Fc receptors on effector cells.

The term "bispecific antibodies" also includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

As used herein, the term "heteroantibodies" refers to two or more antibodies, antibody binding fragments (e.g., Fab), derivatives therefrom, or antigen binding regions linked together, at least two of which have different specificities. These different specificities include a binding specificity for an Fc receptor on an effector cell, and a binding specificity for an antigen or epitope on a target cell, e.g., a tumor cell.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, a "heterohybrid antibody" refers to an antibody having a light and heavy chains of different organismal origins. For example, an antibody having a human heavy chain associated with a murine light chain is a heterohybrid antibody. Examples of heterohybrid antibodies include chimeric and humanized antibodies, discussed supra.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

Anti-CD30 Antibodies

Antibodies against CD30 are well known in the art, e.g., 5F11, HeFi-1, C10, M44, AC10, Ber-H2, HRS-1, HRS-3, HRS-4, Ki-1, Ki-2, Ki-3, Ki-4, Ki-5, Ki-6, Ki-7, IRac, and M67. Preferably, an antibody used in a method of the present invention is chimeric, humanized or human. In a particular embodiment, the antibody is a fully human antibody. Preferred antibodies for use in a method of the invention are characterized by particular functional features or properties of the antibodies. For example, the antibodies bind specifically to human CD30 with high affinity, and preferably exhibit one or more of the following characteristics:

a) a binding affinity to CD30 with an affinity constant of at least about $10^7$ $M^{-1}$, preferably about $10^8$ $M^{-1}$, and more preferably, about $10^9$ $M^{-1}$ to $10^{10}$ $M^{-1}$ or higher;

b) an association constant ($K_{assoc}$) with CD30 of at least about $10^3$, more preferably about $10^4$ and most preferably about $10^5$ $M^{-1}S^{-1}$;

c) a dissociation constant ($K_{dis}$) from CD30 of about $10^{-3}$ $s^{-1}$, preferably about $10^{-4}$ $s^{-1}$, more preferably, $10^{-5}$ $s^{-1}$, and most preferably, $10^{-6}$ $s^{-1}$;

d) the ability to opsonize a cell expressing CD30;

e) the ability to inhibit growth and/or mediate phagocytosis and killing of cells expressing CD30 (e.g., a tumor cell) in the presence of human effector cells at a concentration of about 10 μg/ml or less (e.g., in vitro); or f) the ability to bind to CD30 and inhibit CD30 function (e.g., CD30 mediated effects) by partially or completely blocking a CD30 ligand binding to CD30 (examples of CD30 ligands include CD153, TRAF1, TRAF2, TRAF3 and TRAF5).

Preferably, the antibody binds to human CD30 with a $K_D$ of $5 \times 10^{-9}$ M or less, binds to human CD30 with a $K_D$ of $4 \times 10^{-9}$ M or less, binds to human CD30 with a $K_D$ of $3.5 \times 10^{-9}$ M or less, binds to human CD30 with a $K_D$ of $3 \times 10^{-9}$ M or less or binds to human CD30 with a $K_D$ of $2.8 \times 10^{-9}$ M or less.

Standard assays to evaluate the binding ability of the antibodies toward CD30 are known in the art, including for example, ELISAs, Western blots and RIAs. Suitable assays are described in detail in the Examples. The binding kinetics (e.g., binding affinity) of the antibodies also can be assessed by standard assays known in the art, such as by Biacore analysis.

Monoclonal Antibodies 17G1, 2H9 and 5F11

Preferred antibodies for use in the invention include the human monoclonal antibodies 17G1, 2H9 and 5F11, which are characterized and described in US Patent Application Publication No. 2004/0006215, which is hereby incorporated by reference in its entirety. The $V_H$ amino acid sequences of 17G1, 2H9 and 5F11 are shown in SEQ ID NOs: 2, 6 and 10, respectively. The $V_L$ amino acid sequences of 17G1, 2H9 and 5F11 are shown in SEQ ID NOs: 4, 8 and 12, respectively.

Given that each of these antibodies can bind to CD30, the $V_H$ and $V_L$ sequences can be "mixed and matched" to create other anti-CD30 binding molecules for use in a method of the invention. CD30 binding of such "mixed and matched" antibodies can be tested using the binding assays described above and in the Examples (e.g., ELISAs). Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one aspect, a method of the invention can employ a monoclonal antibody, or antigen binding portion thereof comprising:

(a) a heavy chain variable region comprising an amino acid sequence selected from the group consisting of SEQ ID NOs: 2, 6 and 10; and (b) a light chain variable region comprising an amino acid sequence selected from the group consisting of SEQ ID NOs: 4, 8 and 12;

wherein the antibody specifically binds CD30, preferably human CD30.

Preferred heavy and light chain combinations include:

(a) a heavy chain variable region comprising the amino acid sequence of SEQ ID NO: 2; and (b) a light chain variable region comprising the amino acid sequence of SEQ ID NO: 4; or (b) a heavy chain variable region comprising the amino acid sequence of SEQ ID NO: 6; and (b) a light chain variable region comprising the amino acid sequence of SEQ ID NO: 8; or (c) a heavy chain variable region comprising the amino acid sequence of SEQ ID NO: 10; and (b) a light chain variable region comprising the amino acid sequence of SEQ ID NO: 12.

In another aspect, antibodies that comprise the heavy chain and light chain CDR1s, CDR2s and CDR3s of 17G1, 2H9 and 5F11, or combinations thereof can be used in the present method. The amino acid sequences of the $V_H$ CDR1s of 17G1, 2H9 and 5F11 are shown in SEQ ID NOs: 16, 28 and 40. The amino acid sequences of the $V_H$ CDR2s of 17G1, 2H9 and 5F11 are shown in SEQ ID NOs: 17, 29 and 41. The amino acid sequences of the $V_H$ CDR3s of 17G1, 2H9 and 5F11 are shown in SEQ ID NOs: 18, 30 and 42. The amino acid sequences of the $V_k$ CDR1 s of 17G1, 2H9 and 5F11 are shown in SEQ ID NOs: 22, 34 and 46. The amino acid sequences of the $V_k$ CDR2s of 17G1, 2H9 and 5F11 are shown in SEQ ID NOs: 23, 35 and 47. The amino acid sequences of the $V_k$ CDR3s of 17G1, 2H9 and 5F11 are shown in SEQ ID NOs: 24, 36 and 48. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to CD30 and that antigen-binding specificity is provided primarily by the CDR1, CDR2, and CDR3 regions, the $V_H$ CDR1, CDR2, and CDR3 sequences and $V_k$ CDR1, CDR2, and CDR3 sequences can be "mixed and matched" (i.e., CDRs from different antibodies can be mixed and match, although each antibody must contain a $V_H$ CDR1, CDR2, and CDR3 and a $V_k$ CDR1, CDR2, and CDR3) to create other anti-CD30 binding molecules for use in the invention. CD30 binding of such "mixed and matched" antibodies can be tested using the binding assays described above and in the Examples (e.g., ELISAs, Biacore analysis). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_k$ CDR sequences are mixed and matched, the CDR1, CDR2 and/or CDR3 sequence from a particular $V_k$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies antibodies 17G1, 2H9 and 5F11.

Accordingly, in another aspect, a method of the invention can employ an isolated monoclonal antibody, or antigen binding portion thereof comprising:

(a) a heavy chain variable region CDR1 comprising an amino acid sequence selected from the group consisting of SEQ ID NOs: 16, 28 and 40;

(b) a heavy chain variable region CDR2 comprising an amino acid sequence selected from the group consisting of SEQ ID NOs: 17, 29 and 41;

(c) a heavy chain variable region CDR3 comprising an amino acid sequence selected from the group consisting of SEQ ID NOs: 18, 30 and 42;

(d) a light chain variable region CDR1 comprising an amino acid sequence selected from the group consisting of SEQ ID NOs: 22, 34 and 46;

(e) a light chain variable region CDR2 comprising an amino acid sequence selected from the group consisting of SEQ ID NOs: 23, 35 and 47; and (f) a light chain variable region CDR3 comprising an amino acid sequence selected from the group consisting of SEQ ID NOs: 24, 36 and 48;

wherein the antibody specifically binds CD30, preferably human CD30.

In a preferred embodiment, the antibody comprises:
(a) a heavy chain variable region CDR1 comprising SEQ ID NO: 16;
(b) a heavy chain variable region CDR2 comprising SEQ ID NO: 17;
(c) a heavy chain variable region CDR3 comprising SEQ ID NO: 18;
(d) a light chain variable region CDR1 comprising SEQ ID NO: 22;
(e) a light chain variable region CDR2 comprising SEQ ID NO: 23; and
(f) a light chain variable region CDR3 comprising SEQ ID NO: 24.

In another preferred embodiment, the antibody comprises:
(a) a heavy chain variable region CDR1 comprising SEQ ID NO: 28;
(b) a heavy chain variable region CDR2 comprising SEQ ID NO: 29;
(c) a heavy chain variable region CDR3 comprising SEQ ID NO: 30;
(d) a light chain variable region CDR1 comprising SEQ ID NO: 34;
(e) a light chain variable region CDR2 comprising SEQ ID NO: 35; and
(f) a light chain variable region CDR3 comprising SEQ ID NO: 36.

In yet another preferred embodiment, the antibody comprises:
(a) a heavy chain variable region CDR1 comprising SEQ ID NO: 40;
(b) a heavy chain variable region CDR2 comprising SEQ ID NO: 41;
(c) a heavy chain variable region CDR3 comprising SEQ ID NO: 42;
(d) a light chain variable region CDR1 comprising SEQ ID NO: 46;
(e) a light chain variable region CDR2 comprising SEQ ID NO: 47; and
(f) a light chain variable region CDR3 comprising SEQ ID NO: 48.

Use of Antibodies Having Particular Germline Sequences

In certain embodiments, an antibody used in a method of the invention comprises a heavy chain variable region from a particular germline heavy chain immunoglobulin gene and/or a light chain variable region from a particular germline light chain immunoglobulin gene.

For example, in preferred embodiments, the monoclonal antibody, or an antigen-binding portion thereof, comprises a heavy chain variable region that is the product of or derived from a human $V_H$ 4-34 gene or a human $V_H$ 3-11 gene, wherein the antibody specifically binds CD30. In other preferred embodiments, the monoclonal antibody, or an antigen-binding portion thereof, comprises a light chain variable region that is the product of or derived from a human $V_K$ L15 gene, a human $V_K$ A27 gene or a human $V_K$ L6 gene, wherein the antibody specifically binds CD30. In yet another preferred embodiment, the invention provides an isolated monoclonal antibody, or antigen-binding portion thereof, wherein the antibody:

(a) comprises a heavy chain variable region that is the product of or derived from a human $V_H$ 4-34 or 3-11 gene (which genes encode the amino acid sequences set forth in SEQ ID NO: 49 and 51, respectively);

(b) comprises a light chain variable region that is the product of or derived from a human $V_K$ L15 or $V_K$ A27 or $V_K$ L6 gene (which genes encode the amino acid sequences set forth in SEQ ID NO: 50, 52 and 53, respectively); and (c) specifically binds to CD30, preferably human CD30.

An example of an antibody having $V_H$ and $V_K$ of $V_H$ 4-34 and $V_K$ L15, respectively, is 5F11. An example of an antibody having $V_H$ and $V_K$ of $V_H$ 3-11 and $V_K$ A27, respectively, is 17G1. An example of an antibody having a $V_H$ and $V_K$ of $V_H$ 4-34 and $V_K$ L6, respectively, is 2H9.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody useful in the invention comprises heavy and light chain variable regions comprising amino acid sequences that are homologous to the amino acid sequences of the preferred antibodies described herein, and wherein the antibodies retain the desired functional properties of the preferred anti-CD30 antibodies.

For example, monoclonal antibodies, or antigen binding portion thereof, useful in a method of the invention comprise a heavy chain variable region and a light chain variable region, wherein:

(a) the heavy chain variable region comprises an amino acid sequence that is at least 80% homologous to an amino acid sequence selected from the group consisting of SEQ ID NOs: 2, 6 and 10;

(b) the light chain variable region comprises an amino acid sequence that is at least 80% homologous to an amino acid sequence selected from the group consisting of SEQ ID NOs: 4, 8 and 12;

(c) the antibody binds to human CD30 with a $K_D$ of $1 \times 10^{-8}$ M or less;

(d) the antibody has an association constant ($K_{assoc}$) with CD30 of at least about $10^3$, more preferably about $10^4$ and most preferably about $10^5$ $M^{-1}S^{-1}$;

(e) the antibody has a dissociation constant ($K_{dis}$) from CD30 of about $10^{-3}$ $s^{-1}$, preferably about $10^{-4}$ $s^{-1}$, more preferably, $10^{-5}$ $s^{-1}$, and most preferably, $10^{-6}$ $s^{-1}$;

(f) the antibody has the ability to opsonize a cell expressing CD30;

(g) the antibody has the ability to inhibit growth and/or mediate phagocytosis and killing of cells expressing CD30 (e.g., a tumor cell) in the presence of human effector cells at a concentration of about 10 µg/ml or less (e.g., in vitro); or (h) the antibody has the ability to bind to CD30 and inhibit CD30 function (e.g., CD30 mediated effects) by partially or completely blocking CD30 ligand binding to CD30 (examples of CD30 ligands include CD153, TRAF1, TRAF2, TRAF3 and TRAF5).

In various embodiments, the antibody can be, for example, a human antibody, a humanized antibody or a chimeric antibody.

In other embodiments, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding SEQ ID NOs: 1, 3, 5, 7, 9 and 11, followed by testing of the encoded altered antibody for retained function (i.e., the functions set forth in (c) and (d) above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at the GCG website), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See the NCBI website.

Antibodies with Conservative Modifications

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 17G1, 2H9 or 5F11), or conservative modifications thereof, and wherein the antibodies retain the desired functional properties of the anti-CD30 antibodies of the invention. Accordingly, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of amino acid sequences of SEQ ID NOs: 18, 30 and 42, and conservative modifications thereof;

(b) the light chain variable region CDR3 sequence comprises an amino acid sequence selected from the group consisting of amino acid sequence of SEQ ID NOs: 24, 36 and 48, and conservative modifications thereof;

(c) the antibody binds to human CD30 with a $K_D$ of $1 \times 10^{-8}$ M or less;

(d) the antibody has an association constant ($K_{assoc}$) with CD30 of at least about $10^3$, more preferably about $10^4$ and most preferably about $10^5$ $M^{-1}S^{-1}$;

(e) the antibody has a dissociation constant ($K_{dis}$) from CD30 of about $10^{-3}$ $s^{-1}$, preferably about $10^{-4}$ $s^{-1}$, more preferably, $10^{-5}$ $s^{-1}$, and most preferably, $10^{-6}$ $s^{-1}$;

(f) the antibody has the ability to opsonize a cell expressing CD30;

(g) the antibody has the ability to inhibit growth and/or mediate phagocytosis and killing of cells expressing CD30 (e.g., a tumor cell) in the presence of human effector cells at a concentration of about 10 µg/ml or less (e.g., in vitro); or (h) the antibody has the ability to bind to CD30 and inhibit CD30 function (e.g., CD30 mediated effects) by partially or completely blocking CD30 ligand binding to CD30 (examples of CD30 ligands include CD153, TRAF1, TRAF2, TRAF3 and TRAF5).

In a preferred embodiment, the heavy chain variable region CDR2 sequence comprises an amino acid sequence selected from the group consisting of amino acid sequences of SEQ ID NOs: 17, 29 and 41, and conservative modifications thereof;

and the light chain variable region CDR2 sequence comprises an amino acid sequence selected from the group consisting of amino acid sequences of SEQ ID NOs: 23, 35 and 47, and conservative modifications thereof. In another preferred embodiment, the heavy chain variable region CDR1 sequence comprises an amino acid sequence selected from the group consisting of amino acid sequences of SEQ ID NOs: 16, 28 and 40, and conservative modifications thereof; and the light chain variable region CDR1 sequence comprises an amino acid sequence selected from the group consisting of amino acid sequences of SEQ ID NOs: 22, 34 and 46, and conservative modifications thereof.

In various embodiments, the antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (c) through (j) above) using the functional assays described herein.

Antibodies that Bind to the Same Epitope as Anti-CD30 Antibodies of the Invention In addition to the antibodies described herein, it is contemplated that a method of the invention can employ antibodies that bind to the same cluster (A, B or C), or more poreferably to the same epitope, on human CD30 as any of the CD30 monoclonal antibodies described (i.e., antibodies that have the ability to cross-compete for binding to CD30 with any of the monoclonal antibodies described herein, e.g., 17G1, 2H9 and 5F11). Such cross-competing antibodies can be identified based on their ability to cross-compete with 17G1, 2H9 or 5F11 in standard CD30 binding assays. For example, BIAcore analysis, ELISA assays or flow cytometry can be used to demonstrate cross-competition with the antibodies of the current invention. The ability of a test antibody to inhibit the binding of, for example, 17G1, 2H9 or 5F11, to human CD30 demonstrates that the test antibody can compete with such antibody for binding to human CD30 and thus binds to the same epitope on human CD30 as such antibody. In a preferred embodiment, the antibody that binds to the same epitope on human CD30 as 17G1, 2H9 or 5F11 is a human monoclonal antibody, which can be prepared and isolated as described herein using methodologies well known in the art.

Engineered and Modified Antibodies

An antibody used in the invention can be prepared using one or more of the $V_H$ and/or $V_L$ sequences from an antibody disclosed herein as starting material to engineer a modified antibody, which modified antibody may have altered properties from an antibody disclosed herein. An antibody can be engineered by modifying one or more residues within one or both variable regions (i.e., $V_H$ and/or $V_L$), for example within one or more CDR regions and/or within one or more framework regions. Additionally, or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated monoclonal antibody, or antigen binding portion thereof, comprising a heavy chain variable region comprising CDR1, CDR2, and CDR3 sequences from 17G1, 2H9 or 5F11, but contain modifications to framework sequences. Thus, such antibodies contain the $V_H$ and $V_L$ CDR sequences of monoclonal antibodies 17G1, 2H9 or 5F11 yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at the MRC website), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference.

Preferred framework sequences for use in the antibodies of the invention are those that are structurally similar to the framework sequences used by selected antibodies of the invention, e.g., similar to the $V_H$ 4-34 framework sequences (SEQ ID NO: 49) and/or the $V_H$ 3-11 framework sequences (SEQ ID NO: 51) and/or the $V_K$ L15 framework sequences (SEQ ID NO: 50) and/or the $V_k$ A27 framework sequence (SEQ ID NO: 52) and/or the $V_K$ L6 framework sequence (SEQ ID NO: 53) used by preferred monoclonal antibodies employed in the invention. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the invention provides isolated anti-CD30 monoclonal antibodies, or antigen binding portions thereof, comprising a heavy chain variable region comprising: (a) a $V_H$ CDR1 region comprising an amino acid sequence selected from the group consisting of SEQ ID NOs: 16, 28 and 40, or an amino acid sequence having one, two, three, four or five amino acid substitutions, deletions or additions as compared to SEQ ID NOs: 16, 28 and 40; (b) a $V_H$ CDR2 region comprising an amino acid sequence selected from the group consisting of SEQ ID NOs: 17, 29 and 41, or an amino acid sequence having one, two, three, four or five amino acid substitutions, deletions or additions as compared to SEQ ID NOs: 17, 29 and 41; (c) a $V_H$ CDR3 region comprising an amino acid sequence selected from the group consisting of SEQ ID NOs: 18, 30 and 42, or an amino acid sequence having one, two, three, four or five amino acid substitutions, deletions or additions as compared to SEQ ID NOs: 18, 30 and 42; (d) a $V_K$ CDR1 region comprising an amino acid sequence selected from the group consisting of SEQ ID NOs: 22, 34 and 46, or an amino acid sequence having one, two, three, four or five amino acid substitutions, deletions or additions as compared to SEQ ID NOs: 22, 34 and 46; (e) a $V_K$ CDR2 region comprising an amino acid sequence selected from the group consisting of SEQ ID NOs: 23, 35 and 47, or an amino acid sequence having one, two, three, four or five amino acid substitutions, deletions or additions as compared to SEQ ID NOs: 23, 35 and 47; and (f) a $V_K$ CDR3 region comprising an amino acid sequence selected from the group consisting of SEQ ID NOs: 24, 36 and 48, or an amino acid sequence having one, two, three, four or five amino acid substitutions, deletions or additions as compared to SEQ ID NOs: 24, 36 and 48.

Engineered antibodies of the invention include those in which modifications have been made to framework residues within $V_H$ and/or $V_K$, e.g. to improve the properties of the antibody. Typically such framework modifications are made to decrease the immunogenicity of the antibody. For example, one known approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in futher detail in U.S. Patent Publication No. 20030153043 by Carr et al.

In addition or alternative to modifications made within the framework or CDR regions, antibodies used in the invention can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered Clq binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180).

Another modification of antibodies that can be used in a method of the invention that can be made includes pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Methods of Engineering Antibodies

As discussed above, the anti-CD30 antibodies having $V_H$ and $V_K$ sequences disclosed herein can be used to create new anti-CD30 antibodies by modifying the VH and/or $V_K$ sequences, or the constant region(s) attached thereto. Thus, in another aspect of the invention, the structural features of an anti-CD30 antibody of the invention, e.g. 17G1, 2H9 or 5F11, are used to create structurally related anti-CD30 antibodies that retain at least one functional property of the antibodies of the invention, such as binding to human CD30. For example, one or more CDR regions of 17G1, 2H9 or 5F11, or mutations thereof, can be combined recombinantly with known framework regions and/or other CDRs to create additional, recombinantly-engineered, anti-CD30 antibodies of the invention, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-CD30 antibody comprising:

(a) providing: (i) a heavy chain variable region antibody sequence comprising a CDR1 sequence selected from the group consisting of SEQ ID NOs: 16, 28 and 40, a CDR2 sequence selected from the group consisting of SEQ ID NOs: 17, 29 and 41, and/or a CDR3 sequence selected from the group consisting of SEQ ID NOs: 18, 30 and 42; and/or (ii) a light chain variable region antibody sequence comprising a CDR1 sequence selected from the group consisting of SEQ ID NOs: 22, 34 and 46, a CDR2 sequence selected from the group consisting of SEQ ID NOs: 23, 35 and 47, and/or a CDR3 sequence selected from the group consisting of SEQ ID NOs: 24, 36 and 48;

(b) altering at least one amino acid residue within the heavy chain variable region antibody sequence and/or the light chain variable region antibody sequence to create at least one altered antibody sequence; and (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-CD30 antibodies described herein, which functional properties include, but are not limited to:

(a) binds to human CD 30 with a $K_D$ of $1 \times 10^{-8}$ M or less;

(b) the light chain variable region comprises an amino acid sequence that is at least 80% homologous to an amino acid sequence selected from the group consisting of SEQ ID NOs: 4, 8 and 12;

(c) the antibody binds to human CD30 with a $K_D$ of $1 \times 10^{-8}$ M or less;

(d) the antibody has an association constant ($K_{assoc}$) with CD30 of at least about $10^3$, more preferably about $10^4$ and most preferably about $10^{-5}$ $M^{-1}$ $S^{-1}$;

(e) the antibody has a dissociation constant ($K_{dis}$) from CD30 of about $10^{-3}$ $s^{-1}$, preferably about $10^{-4}$ $s^{-1}$, more preferably, $10^{-5}$ $s^{-1}$, and most preferably, $10^{-6}$ $s^{-1}$;

(f) the antibody has the ability to opsonize a cell expressing CD30;

(g) the antibody has the ability to inhibit growth and/or mediate phagocytosis and killing of cells expressing CD30 (e.g., a tumor cell) in the presence of human effector cells at a concentration of about 10 µg/ml or less (e.g., in vitro); or (h) the ability to bind to CD30 and inhibit CD30 function (e.g., CD30 mediated effects) by partially or completely blocking CD30 ligand binding to CD30 (examples of CD30 ligands include CD153, TRAF1, TRAF2, TRAF3 and TRAF5).

The functional properties of the altered antibodies can be assessed using standard assays available in the art and/or described herein, such as those set forth in the Examples (e.g., flow cytometry, binding assays).

In certain embodiments of the methods of engineering antibodies of the invention, mutations can be introduced randomly or selectively along all or part of an anti-CD30 antibody coding sequence and the resulting modified anti-CD30 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Nucleic acid molecules that encode certain of the antibodies useful in the invention are described herein (SEQ ID NOs: 1, 3, 5, 7, 9, and 11). The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of the invention are those encoding the VH and VL sequences of the 17G1, 2H9 or 5F11 monoclonal antibodies. DNA sequences encoding the VH sequences of 17G1, 2H9 and 5F11 are shown in SEQ ID NOs: 1, 5, and 9, respectively. DNA sequences encoding the VL sequences of 17G1, 2H9 and 5F11 are shown in SEQ ID NOs: 3, 7 and 11, respectively.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Production of Monoclonal Antibodies of the Invention

Monoclonal antibodies (mAbs) useful in the present invention can be produced by a variety of techniques, including conventional monoclonal antibody methodology, e.g., the standard somatic cell hybridization technique of Kohler and Milstein (1975) *Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known. Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of the invention are human monoclonal antibodies. Such human monoclonal antibodies directed against CD30 can be generated using transgenic or transchromosomic mice carrying parts of the human immune system rather than the mouse system. These transgenic and transchromosomic mice include mice referred to herein as HuMAb Mouse® and KM Mouse®, respectively, and are collectively referred to herein as "human Ig mice." These mice are well-known in the art (see e.g., Lonberg, et al. (1994) Nature 368(6474): 856-859; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). The preparation and use of HuMab mice, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.)

In another embodiment, human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM Mice®", are described in detail in PCT Publication WO 02/43478 to Ishida et al.

Still further, alternative transgenic animal systems expressing human immunoglobulin genes are available in the art and can be used to raise anti-CD30 antibodies used in the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-CD30 antibodies used in the invention. For example, mice carrying both a human heavy chain transchromosome and a human light chain tranchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-CD30 antibodies used in the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies used in the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

Immunization of human Ig mice for raising human antibodies is described in detail in US Patent Application Publication No. 2004/0006215, which is hereby incorporated by reference in its entirety. Detailed procedures to generate fully human monoclonal antibodies to CD30 are also described therein.

Generation of Hybridomas Producing Human Monoclonal Antibodies of the Invention

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. Such methodologies are well known in the art and are described in US 2004/0006125

Generation of Transfectomas Producing Monoclonal Antibodies of the Invention

Antibodies used in the invention can be produced in a host cell transfectoma system using, for example, a combination of recombinant DNA techniques and gene transfection methods that are well known in the art (e.g., Morrison, S. (1985) Science 229:1202), and described in detail in US 2004/0006125.

Characterization of Binding of Human Monoclonal Antibodies to CD30

To characterize binding of human monoclonal CD30 antibodies of the invention, sera from immunized mice can be tested, for example, by ELISA. In a typical (but non-limiting) example of an ELISA protocol, microtiter plates are coated with purified CD30 at 0.25 µg/ml in PBS, and then blocked with 5% bovine serum albumin in PBS. Dilutions of plasma from CD30-immunized mice are added to each well and incubated for 1-2 hours at 37° C. The plates are washed with PBS/Tween and then incubated with a goat-anti-human IgG Fc-specific polyclonal reagent conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with CD30 immunogen. Hybridomas that bind with high avidity to CD30 will be subcloned and further characterized. One clone from each hybridoma, which retains the reactivity of the parent cells (by ELISA), can be chosen for making a 5-10 vial cell bank stored at −140° C., and for antibody purification.

To purify human anti-CD30 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected human anti-CD30 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using CD30 coated-ELISA plates as described above. Biotinylated MAb binding can be detected with a strep-avidin-alkaline phosphatase probe.

To determine the isotype of purified antibodies, isotype ELISAs can be performed. For example, wells of microtiter plates can be coated with 10 µg/ml of anti-human Ig overnight at 4° C. After blocking with 5% BSA, the plates are reacted with 10 µg/ml of monoclonal antibodies or purified isotype controls, at ambient temperature for two hours. The wells can then be reacted with either human IgG1 or human IgM-specific alkaline phosphatase-conjugated probes. Plates are developed and analyzed as described above.

In order to demonstrate binding of monoclonal antibodies to live cells expressing the CD30, flow cytometry can be used. In a typical (but non-limiting) example of a flow cytometry protocol, cell lines expressing CD30 (grown under standard growth conditions) are mixed with various concentrations of monoclonal antibodies in PBS containing 0.1% BSA and 20% mouse serum, and incubated at 37° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-CD30 human IgGs can be further tested for reactivity with CD30 antigen by Western blotting. For example, cell extracts from cells expressing CD30 can be prepared and subjected to sodium dodecyl sulfate (SDS) polyacrylamide gel electrophoresis. After electrophoresis, the separated antigens will be transferred to nitrocellulose membranes, blocked with 20% mouse serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Phagocytic and Cell Killing Activities of Human Monoclonal Antibodies to CD30

In addition to binding specifically to CD30, human monoclonal anti-CD30 antibodies can be tested for their ability to mediate phagocytosis and killing of cells expressing CD30. The testing of monoclonal antibody activity in vitro will provide an initial screening prior to testing in vivo models. Briefly, polymorphonuclear cells (PMN), or other effector cells, from healthy donors can be purified by Ficoll Hypaque density centrifugation, followed by lysis of contaminating erythrocytes. Washed PMNs, can be suspended in RPMI supplemented with 10% heat-inactivated fetal calf serum and mixed with $^{51}Cr$ labeled cells expressing CD30, at various ratios of effector cells to tumor cells (-effector cells:tumor cells). Purified human anti-CD30 IgGs can then be added at various concentrations. Irrelevant human IgG can be used as negative control. Assays can be carried out for 4-18 hours at 37° C. Samples can be assayed for cytolysis by measuring $^{51}Cr$ release into the culture supernatant. Anti-CD30 monoclonal can also be tested in combinations with each other to determine whether cytolysis is enhanced with multiple monoclonal antibodies.

Human monoclonal antibodies which bind to CD30 also can be tested in an in vivo model (e.g., in mice) to determine their efficacy in mediating phagocytosis and killing of cells expressing CD30, e.g., tumor cells. These antibodies can be selected, for example, based on the following criteria, which are not intended to be exclusive:

1.) binding to live cells expressing CD30;
2.) high affinity of binding to CD30;
3.) binding to a unique epitope on CD30 (to eliminate the possibility that monoclonal antibodies with complimentary activities when used in combination would compete for binding to the same epitope);
4.) opsonization of cells expressing CD30;
5.) mediation of growth inhibition, phagocytosis and/or killing of cells expressing CD30 in the presence of human effector cells.

Preferred human monoclonal antibodies of the invention meet one or more, and preferably all, of these criteria. In a particular embodiment, the human monoclonal antibodies are used in combination, e.g., as a pharmaceutical composition comprising two or more anti-CD30 monoclonal antibodies or fragments thereof. For example, human anti-CD30 monoclonal antibodies having different, but complementary activities can be combined in a single therapy to achieve a desired therapeutic or diagnostic effect. An illustration of this would be a composition containing an anti-CD30 human monoclonal antibody that mediates highly effective killing of target cells in the presence of effector cells, combined with another human anti-CD30 monoclonal antibody that inhibits the growth of cells expressing CD30.

Bispecific/Multispecific Molecules Which Bind to CD30

In yet another embodiment of a method of the invention, human monoclonal antibodies to CD30, or antigen-binding portions thereof, can be derivatized or linked to another functional molecule, e.g., another peptide or protein (e.g., an Fab' fragment) to generate a bispecific or multispecific molecule which binds to multiple binding sites or target epitopes. For example, an antibody or antigen-binding portion of the invention can be functionally linked (e.g., by chemical coupling, genetic fusion, noncovalent association or otherwise) to one or more other binding molecules, such as another antibody, antibody fragment, peptide or binding mimetic. Bispecific molecules useful in the present invention include those described in US 2004/0006215. In a particular embodiment, the bispecific antibody is H22xKi4, which is also described in US 2004/0006215.

An "effector cell specific antibody" as used herein refers to an antibody or functional antibody fragment that binds the Fc receptor of effector cells. Preferred antibodies for use in the subject invention bind the Fc receptor of effector cells at a site which is not bound by endogenous immunoglobulin.

As used herein, the term "effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Some effector cells express specific Fc receptors and carry out specific immune functions. In preferred embodiments, an effector cell is capable of inducing antibody-dependent cell-mediated cytotoxicity (ADCC), e.g., a neutrophil capable of inducing ADCC. For example, monocytes, macrophages, which express FcR are involved in specific killing of target cells and presenting antigens to other components of the immune system, or binding to cells that present antigens. In other embodiments, an effector cell can phagocytose a target antigen, target cell, or microorganism. The expression of a particular FcR on an effector cell can be regulated by humoral factors such as cytokines. For example, expression of FcγRI has been found to be up-regulated by interferon gamma (IFN-γ). This enhanced expression increases the cytotoxic activity of FcγRI-bearing cells against targets. An effector cell can phagocytose or lyse a target antigen or a target cell.

"Target cell" shall mean any undesirable cell in a subject (e.g., a human or animal) that can be targeted by a composition (e.g., a human monoclonal antibody, a bispecific or a multispecific molecule) of the invention. In preferred embodiments, the target cell is a cell expressing or overexpressing CD30, e.g., a CD30 positive lymphoma. Cells expressing CD30 typically include tumor cells, such as bladder, breast, colon, kidney, ovarian, prostate, renal cell, squamous cell, lung (non-small cell), and head and neck tumor cells. Other target cells include synovial fibroblast cells.

Chimeric mouse-human monoclonal antibodies (i.e., chimeric antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559).

The chimeric antibody can be further humanized by replacing sequences of the Fv variable region which are not directly involved in antigen binding with equivalent sequences from human Fv variable regions. General reviews of humanized chimeric antibodies are provided by Morrison, S. L., 1985, Science 229:1202-1207 and by Oi et al., 1986, BioTechniques 4:214. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution U.S. Pat. No. 5,225,539; Jones et al. 1986 Nature 321:552-525; Verhoeyan et al. 1988 Science 239:1534; and Beidler et al. 1988 J. Immunol. 141:4053-4060.

All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method, which is capable of replacing at least a portion of a CDR of a human antibody with a CDR derived from a non-human antibody. Winter describes a method which may be used to prepare the humanized antibodies of the present invention (UK Patent Application GB 2188638A, filed on Mar. 26, 1987), the contents of which is expressly incorporated by reference. The human CDRs may be replaced with non-human CDRs using oligonucleotide site-directed mutagenesis as described in International Application WO 94/10332 entitled, Humanized Antibodies to Fc Receptors for Immunoglobulin G on Human Mononuclear Phagocytes.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances. Antibodies in which amino acids have been added, deleted, or substituted are referred to herein as modified antibodies or altered antibodies.

The term modified antibody is also intended to include antibodies, such as monoclonal antibodies, chimeric antibodies, and humanized antibodies which have been modified by, e.g., deleting, adding, or substituting portions of the antibody. For example, an antibody can be modified by deleting the constant region and replacing it with a constant region meant to increase half-life, e.g., serum half-life, stability or affinity of the antibody. Any modification is within the scope of the invention so long as the bispecific and multispecific molecule has at least one antigen binding region specific for an FcγR and triggers at least one effector function.

Bispecific and multispecific molecules of the present invention can be made using chemical techniques (see e.g., D. M. Kranz et al. (1981) Proc. Natl. Acad. Sci. USA 78:5807), "polydoma" techniques (See U.S. Pat. No. 4,474,893, to Reading), or recombinant DNA techniques.

In particular, bispecific and multispecific molecules of the present invention can be prepared by conjugating the constituent binding specificities, e.g., the anti-FcR and anti-CD30 binding specificities, using methods known in the art and described in the examples provided herein. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described by Paulus (Behring Ins. Mitt. (1985) No. 78, 118-132); Brennan et al. (Science (1985) 229:81-83), and Glennie et al. (J. Immunol. (1987) 139: 2367-2375). Preferred conjugating agents are SATA and sulfo-SMCC, both available from Pierce Chemical Co. (Rockford, Ill.).

When the binding specificities are antibodies (e.g., two humanized antibodies), they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific and multispecific molecule is a MAb×MAb, MAb×Fab, Fab×F(ab')$_2$ or ligand×Fab fusion protein. A bispecific and multispecific molecule of the invention, e.g., a bispecific molecule can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing bi- and multspecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific and multispecific molecules to their specific targets can be confirmed by enzyme-linked immunosorbent assay (ELISA), a radioimmunoassay (RIA), FACS analysis, a bioassay (e.g., growth inhibition), or a Western Blot Assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Immunoconjugates

In another aspect, antibodies used in the present invention can be conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies used in the invention via linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Antibodies used in the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium[177]. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates used in a method of the invention can modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Proteasome Inhibitors

The present invention requires administration of an inhibitor of NF-κB either through direct or indirect inhibition, in combination with an anti-CD30 antibody in order to treat CD30 positive lymphomas. Proteasome inhibitors are useful in a method of the present invention. In a particular embodiment, the proteosome inhibitor decreases or blocks the chymotrypsin-like activity of the 26S proteasome found in mammalian cells. The 26S proteasome is a large protein complex that degrades ubiquitinated proteins and indirectly activates the NF-κB pathway. Selective inhibition of proteasome activity has numerous effects that can be relevant in cancer treatment, including attenuating the activity of NF-κB, the transcription factor that controls cellular inflammatory response, and inhibiting the activity of bcl-2, a gene involved in cell survival. Elevated NF-κB and bcl-2 activities allow cancer cells to defend themselves against treatment with standard chemotherapy agents. By blocking the normal function of NF-κB and bcl-2, a proteasome inhibitor can cause the death of cancer cells. Thus, compounds which reduce the activity of NF-κB directly or indirectly, such as through inhibiting the activity of the 26S proteasome, can be used in a method of the present invention.

Inhibitors of proteasome activity, and methods for their manufacture, are well-known in the art, e.g., the boronic acid and ester compounds described in U.S. Pat. Nos. 5,780,454, 6,066,730, 6,083,903, 6,297,217, 6,465,433, 6,548,668, 6,617,317, and 6,747,150. Other proteasome inhibitor compounds include peptide aldehydes, e.g., ALLnL (N-acetyl-leucinyl-leucynil-norleucynal, MG101), LLM (N-acetyl-leucinyl-leucynil-methional), Z-LLnV (carbobenzoxyl-leucinyl-leucynil-norvalinal, MG 115), Z-LLL (carbobenzoxyl-leucinyl-leucynil-leucynal, MG132), Lactacystine, b-lactone, Boronic Acid Peptides, Ubiquitin Ligase Inhibitors, Cyclosporin A, FK506 (Tacrolimus) and Deoxyspergualin.

In addition, compounds can be tested for their ability to inhibit the activation of NF-κB by means of a DNA binding assay (Palombella, et al., Cell 78.773 (1994)). For example, whole-cell extracts can be prepared from untreated or TNF-α treated cells that have been pretreated for 1 hour with the test compound. The DNA binding activity of NF-κB can be measured by an electrophoretic mobility shift assay using the PRDII probe from the human IFN-β gene promoter. As an indirect measure of NF-κB activation, the cell-surface expression of E-selectin, I-CAM-1, and V-CAM-1 on primary human umbilical vein endothelial cells (HUVECs) can be determined by means of a cell surface fluorescent immunobinding assay. Because E-selectin, I-CAM-1, and V-CAM-1 are under the regulatory control of NF-κB, inhibition of NF-κB activation results in reduced levels of these adhesion molecules on the cell surface.

In a particular embodiment of the invention, the proteasome inhibitor is bortezomib (Millenium Pharmaceuticals; Cambridge, Mass.), which is a reversible inhibitor of the chymotrypsin-like activity of the 26S proteasome and is described in U.S. Pat. No. 5,780,454. In another embodiment, the proteasome inhibitor is MG-132 (Calbiochem, Calif.).

As used herein, the phrase "a compound that inhibits NF-κB" is used to mean any compound that either directly or indirectly affects the activity of NF-κB so that activity of NF-κB is decreased or blocked in order to allow apoptosis. Proteasome inhibitors described above are examples of such compounds which indirectly affect the activity of NF-κB.

Pharmaceutical Compositions

Methods of the present invention employ (i) a composition, e.g., a pharmaceutical composition, containing one or a combination of anti-CD30 monoclonal antibodies, or antigen-binding portion(s) thereof, of the present invention, formulated together with a pharmaceutically acceptable carrier and (ii) a composition, e.g., a pharmaceutical composition, containing a proteasome inhibitor formulated together with a pharmaceutically acceptable carrier. Antibody compositions may include one or a combination of (e.g., two or more different) antibodies, or immunoconjugates or bispecific molecules, as described herein. For example, an antibody pharmaceutical composition can comprise a combination of antibodies (or immunoconjugates or bispecifics) that bind to different epitopes on CD30 or that have complementary activities.

The pharmaceutical compositions used in the invention also can be futher combined with additional agents. For example, if desirable, the combination therapy of the invention, i.e., antibody and proteasome inhibitor can include at least one other anti-tumor or cytostatic or cytotoxic agent. Examples of additional therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjuage, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), diethylenetriaminepentaacetic acid (DTPA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more typically 0.01 to 25 mg/kg, of the host body weight. For example dosages can be 0.3 mg/kg body weight, 1 mg/kg body weight, 3 mg/kg body weight, 5 mg/kg body weight or 10 mg/kg body weight, 12.5 mg/kg body weight, 15 mg/kg body weight, or 20 mg/kg body weight, or 25 mg/kg body weight or within the range of 1-25 mg/kg. An exemplary treatment regime entails administration of the antibody and proteasome inhibitor compositions simultaneously once per week, once every two weeks, once every three weeks, once every four weeks, once a month, once every 3 months or once every three to 6 months. Preferred dosage regimens for an anti-CD30 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

For administration of the proteasome inhibitor, the dosage ranges from about 0.0001 to 100 mg/kg, and more typically 0.01 to 25 mg/kg, of the host body weight. For example dosages can be 0.3 mg/kg body weight, 1 mg/kg body weight, 3 mg/kg body weight, 5 mg/kg body weight or 10 mg/kg body weight, 12.5 mg/kg body weight, 15 mg/kg body weight, or 20 mg/kg body weight, or within the range of 1-20 mg/kg. An exemplary treatment regime entails administration once per week, once every two weeks, once every three weeks, once every four weeks, once a month, once every 3 months or once every three to 6 months. Preferred dosage regimens for an anti-CD30 proteasome inhibitor of the invention include 1 mg/kg body weight or 3 mg/kg body weight via intravenous administration, with the proteasome inhibitor being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody and proteasome inhibitor can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-CD30 antibody and a proteasome inhibitor used in the invention preferably results in a decrease in severity of disease symptoms, an increase in frequency and duration of disease symptom-free periods, or a prevention of impairment or disability due to the disease affliction. For example, for the treatment of CD30 positive tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors, e.g., as described in the Example, infra. Alternatively, this property of a composition can be evaluated by examining the ability of the compound to inhibit, such inhibition in vitro by assays known to the skilled practitioner. Such assays are described in the Example, infra., e.g., XTT-Assay, reported gene assay TUNEL assay, Annexin. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The antibody and proteaseom inhibitor compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399, 163; 5,383,851; 5,312,335; 5,064,413; 4,941,880; 4,790,824; or 4,596,556. Examples of well-known implants and modules useful in the present invention include: U.S. Pat. No. 4,487, 603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p 120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the desired area, e.g., the site of inflammation or infection, or the site of a tumor. The composition must be fluid to the extent that easy syringability exists. It must be stable under the conditions of manufacture and storage and must be preserved against the contaminating action of microorganisms such as bacteria and fungi.

A "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit cancer can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

For example, the human antibodies, antibody compositions and methods of the present invention can be used to treat a subject with a tumorigenic disorder, e.g., a disorder characterized by the presence of tumor cells expressing CD30 including, for example, Hodgkin's disease, anaplastic large cell lymphoma (ALCL), adult T-cell lymphoma. (ATL), angioimmunoblastic lymphadenopathy (AILD)-like T cell lymphoma, HIV associated body cavity based lymphomas, Embryonal Carcinomas, undifferentiated carcinomas of the rhino-pharynx (e.g., Schmincke's tumor), Castleman's disease, Kaposi's Sarcoma and other T-cell or B-cell lymphomas. The human antibodies, antibody compositions and the methods of the present invention can also be used to treat a subject with other disorders, e.g., autoimmune diseases, including, for example, Rheumatoid arthritis, Systemic Lupus Erythematosus, Systemic Sclerosis, Atopic Dermatitis, Graves' disease, Hashimoto's thyroiditis, Wegner's granulomatosis, Omen's syndrome, chronic renal failure, acute infectious mononucleosis, HIV and herpes virus associated diseases.

In a particular embodiment, a method of the present invention is used in vivo to treat, prevent or diagnose a variety of CD30-related diseases. Examples of CD30-related diseases include, among others, cancer, Hodgkin's disease, non-Hodgkin's lymphoma, anaplastic large cell lymphoma (ALCL), adult T-cell lymphoma. (ATL), angioimmunoblastic lymphadenopathy (AILD)-like T cell lymphoma, HIV associated body cavity based lymphomas, Embryonal Carcinomas, undifferentiated carcinomas of the rhino-pharynx (e.g., Schmincke's tumor), Castleman's disease, Kaposi's Sarcoma and other T-cell or B-cell lymphomas. Other CD30 mediated diseases include among others, autoimmune diseases, Rheumatoid arthritis, Systemic Lupus Erythematosus, Systemic Sclerosis, Atopic Dermatitis, Graves' disease, Hashimoto's thyroiditis, Wegner's granulomatosis, Omen's syndrome, chronic renal failure, acute infectious mononucleosis, HIV and herpes virus associated diseases.

In a particular embodiment, a method of the present invention is used to treat or to prevent Hodgkin's disease (HD), as the antibodies limit the role that CD30 plays in the progression of HD and other tumorigenic diseases. Hodgkin's disease is a type of lymphoma. Lymphomas are cancers that develop in the lymph system, part of the body's immune system. Because there is lymph tissue in many parts of the body, HD can start in almost any part of the body. The cancer can spread to almost any organ or tissue in the body, including the liver, bone marrow (the spongy tissue inside the large bones of the body that makes blood cells), and the spleen. Elevated expression of CD30 in Hodgkin's and Reed-Sternberg cells has been reported to correlate with the differential diagnosis of HD. Accordingly, CD30 inhibiting antibodies in combination with proteasome inhibitors can be used to prevent or block the effects of CD30 which lead to HD and, thus, can be used to prevent or treat this disease.

Human antibodies (e.g., human monoclonal antibodies, multispecific and bispecific molecules) in combination with proteasome inhibitors also can be used to block or inhibit other effects of CD30. For example, it is known that CD30 is also regularly expressed by a variety of non-Hodgkin's lymphoma subtypes. Accordingly, yet another use for the method of the invention includes the prevention or treatment of diseases involving non-Hodgkin's lymphomas. These diseases include Burkitt's lymphoma, anaplastic large-cell lymphomas (ALCL), cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), and entroblastic/centrocytic (cb/cc) follicular lymphomas cancers.

In another particular embodiment, a method of the present invention can be used to block or inhibit yet other effects of CD30. For example, it is also known that soluble CD30 is regularly shed from the surface of cells expressing CD30. Elevated sCD30 levels have been reported in the serum of patients with a variety of tumorigenic and autoimmune disorders. Accordingly, yet another use for the anti-CD3-antibodies in combination with the proteasome inhibitors includes the prevention or treatment of diseases involving blocking or inhibiting of shedding of sCD30. Such diseases include, but are not limited to, Rheumatoid arthritis, Systemic Lupus Erythematosus, Systemic Sclerosis, Atopic Dermatitis, Graves' disease, Hashimoto's thyroiditis, Wegner's granulomatosis, and Omen's syndrome.

Suitable routes of administering the antibody and proteasome inhibitor pharmaceutical compositions in a method of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-CD30 antibodies and proteasome inhibitors used in the invention can be co-administered with one or more other therapeutic agents, e.g., an cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/m$^2$ dose once every four weeks and adriamycin is intravenously administered as a 60-75 mg/m$^2$ dose once every 21 days. Co-administration with other chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Target-specific effector cells, e.g., effector cells linked to compositions (e.g., human antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells, can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing CD30, and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-CD30 antibodies linked to anti-Fc-gamma RI or anti-CD3 may be used in conjunction with IgG- or IgA-receptor specific binding agents.

Bispecific and multispecific molecules of the invention can also be used to modulate FcγR or FcαR levels on effector cells, such as by capping and elimination of receptors on the cell surface. Mixtures of anti-Fc receptors can also be used for this purpose.

The antibody and proteasome inhibitor pharmaceutical compositions used in the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., human antibodies, multispecific and bispecific molecules) of the invention can also be lysed by complement. In yet another embodiment, the compositions of the invention do not activate complement.

The compositions (e.g., human antibodies, multispecific and bispecific molecules and immunoconjugates) of the invention can also be administered together with complement. Accordingly, within the scope of the invention are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of the invention and the complement or serum can be administered separately.

Accordingly, patients treated with antibody and proteasome inhibitor compositions of the invention can be additionally administered (prior to, simultaneously with, or following administration of a human antibody of the invention) with another therapeutic agent, such as a cytotoxic or radiotoxic agent, which enhances or augments the therapeutic effect of the human antibodies.

In other embodiments, the subject can be additionally treated with an agent that modulates, e.g., enhances or inhibits, the expression or activity of Fcγ or Fcα receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

In another embodiment, the subject can be additionally treated with a lymphokine preparation. Cancer cells which do not highly express CD30 can be induced to do so using lymphokine preparations. Lymphokine preparations can cause a more homogeneous expression of CD30s among cells of a tumor which can lead to a more effective therapy. Lymphokine preparations suitable for administration include interferon-gamma, tumor necrosis factor, and combinations thereof. These can be administered intravenously. Suitable dosages of lymphokine are 10,000 to 1,000,000 units/patient.

The antibody and proteasome inhibitor compositions used in the invention can also be used to target cells expressing FcγR or CD30, for example for labeling such cells. For such use, the binding agent can be linked to a molecule that can be detected. Thus, the invention provides methods for localizing ex vivo or in vitro cells expressing Fc receptors, such as FcγR, or CD30. The detectable label can be, e.g., a radioisotope, a fluorescent compound, an enzyme, or an enzyme co-factor.

In other embodiments, the invention provides methods for treating an CD30 mediated disorder in a subject, e.g., Hodgkin's disease, adult T-cell lymphoma, infectious mononucleosis, and Systemic Lupus Erythematosus, by administering to the subject the human antibodies described above. Such antibodies and derivatives thereof are used to inhibit CD30 induced activities associated with certain disorders, e.g., proliferation and differentiation. Other CD30 induced activities which can be inhibited by the antibodies of the present invention include increased production of sCD30, increased expression of IL-4 and increased production of the Th2 phenotype. By contacting the antibody with CD30 (e.g., by administering the antibody to a subject), the ability of CD30 to induce such activities is inhibited and, thus, the associated disorder is treated. Preferred antibodies bind to epitopes which are specific to CD30 and, thus, advantageously inhibit CD30 induced activities, but do not interfere with the activity of structurally related surface antigens, such as NGFR, CD27 and CD40.

Accordingly, in another embodiment, the present invention provides a method for treating or preventing a tumorigenic disorder mediated by human CD30, e.g., Hodgkin's disease, non-Hodgkin's lymphoma, anaplastic large cell lymphoma (ALCL), adult T-cell lymphoma. (ATL), angioimmunoblastic lymphadenopathy (AILD)-like T cell lymphoma, HIV associated body cavity based lymphomas, Embryonal Carcinomas, undifferentiated carcinomas of the rhino-pharynx (e.g., Schmincke's tumor), Castleman's disease, Kaposi's Sarcoma and other T-cell or B-cell lymphomas. The method involves administering to a subject a antibody composition of the present invention in an amount effective to treat or prevent the disorder. The antibody composition can be administered alone or along with another therapeutic agent, such as a cytotoxic or a radiotoxic agent which acts in conjunction with or synergistically with the antibody composition to treat or prevent the CD30 mediated disease. In a particularly preferred embodiment, the present invention provides a method for treating Hodgkin's disease. In yet another particularly preferred embodiment, the present invention provides a method for treating ALCL.

In another embodiment, the present invention provides a method for treating or preventing an autoimmune disorder mediated by human CD30, e.g., Rheumatoid arthritis, Systemic Lupus Erythematosus, Systemic Sclerosis, Atopic Dermatitis, Graves' disease, Hashimoto's thyroiditis, Wegner's granulomatosis, Omen's syndrome, chronic renal failure, acute infectious mononucleosis, HIV and herpes virus associated diseases. The method involves administering to a subject an antibody and proteasome inhibitor compositions of the present invention in an amount effective to treat or prevent the disorder. The compositions can be administered alone or along with another therapeutic agent, such as an immunosuppressant which acts in conjunction with or synergistically with the antibody composition to treat or prevent the CD30 mediated disease.

In yet another embodiment, immunoconjugates of the invention can be used a proteasome inhibitor to target compounds (e.g., therapeutic agents, labels, cytotoxins, radiotoxoins immunosuppressants, etc.) to cells which have CD30 bound to their surface (e.g., membrane bound or bound to CD30 receptor) by linking such compounds to the antibody. Thus, the invention also provides methods for localizing ex vivo or in vitro cells expressing CD30 and CD30 receptor, such as Hodgkin's cells or Reed-Sternberg cells (e.g., with a detectable label, such as a radioisotope, a fluorescent compound, an enzyme, or an enzyme co-factor). Alternatively, the immunoconjugates can be used to kill cells which have CD30 bound to their surface (e.g., membrane bound or bound to CD30 receptor) by targeting cytotoxins or radiotoxins to CD30.

The present invention is further illustrated by the following examples which should not be construed as further limiting.

Example

Human Anti-CD30 Antibody Activates NF-κB and Sensitizes Lymphoma Cells to Proteasome Inhibitor-Induced Apoptosis 5F11 is a fully human monoclonal antibody directed against CD30 that has shown to be effective in inducing growth arrest or killing of CD30-expressing lymphoma cell lines both in vitro and in vivo. However, some cell lines were shown to demonstrate partial or even complete resistance to 5F11-induced apoptosis. In the present Example, the efficacy of the combination of 5F11 and bortezomib, a proteasome inhibitor with antitumoral activity, was tested. Using XTT viability tests, TUNEL assays and FACS analysis a synergistic cytotoxic effect of 5F11 and bortezomib was seen against Hodgkin cell lines (L540, L428) and the CD30 expressing ALCL Karpas 299. Moreover the growth of subcutaneous L540 derived human Hodgkin tumors in SCID mice was inhibited by 5F11 in combination with bortezomib, whereas the combined effect of each agent alone was less effective. The synergy of 5F11 and bortezomib seen in vitro depends on the schedule used and is only seen when the two are added simultaneously or when the cells are first pre-incubated with 5F11.

Material and Methods

Cell Lines

The Hodgkin-derived cell lines (L540 and L428), the anaplastic large cell lymphoma derived Karpas299 and the CD30-negative acute lymphatic leukemia-derived cell line REH, were obtained from the German Collection of Microorganisms and Cell Cultures (DMSZ) and have been described previously. All cells were cultivated in RPMI-1640 medium, supplemented with 10% (v/v) heat-inactivated fetal calf serum (FCS), 50 µg/ml streptomycine, 50 µg/ml penicilline and 2 mM L-glutamine at 37° C. in a 5% CO2 atmosphere. Medium was replaced twice weekly and 24 h before performing the assays. Assays were performed in FCS and antibiotic-free medium (plain medium).

Antibodies, Reagents and Plasmids

Anti-CD30 antibody 5F11 was kindly provided by Medarex Inc. (Bloomsbury, N.J.). Goat anti-human Fc antibody (GaH) was purchased from Dianova/Jackson, USA. The proteasome inhibitor MG-132 was purchased from Calbiochem, CA and bortezomib (Velcade) from Millennium, Mass.

Rabbit-anti p65-IgG and FITC-labeled mouse-anti-rabbit-IgG were obtained from Santa Cruz, USA. Expression vectors and reporter constructs to measure NF-κB activation (NF-κB-luc, IkBaM) were from Clontech, BD Biosciences, CA (Mercury Vector Set).

XTT-Assay $2\times10^4$ cells were incubated in each well of a 96-well microtiter-plate (tissue culture grade flat bottom). Cells were pre-incubated at 37° C. with 5 µg/ml anti-CD30-antibody 5F11 and 25 µg/ml of crosslinking antibody goat-anti-human (GaH). After 30 min incubation, bortezomib was added in the concentration indicated up to a total volume of 200 µl per well, and cells were incubated 48 h at 37° C. Each measurement was done in triplicate. The incubation time and concentrations in the control wells (each antibody alone and in combination, bortezomib in the absence of 5F11) were as described above.

To measure the cell viability, cells were pulsed with fresh plain media containing 1.49 mM XTT and 0.025 mM phenazin-ethosulfate for four hours and the absorbance was measured at 450 nm vs. 650 nm with an ELISA reader (Bio-Tek, Winooski, Vt., USA). The concentration required to achieve 50% reduction of tetrazolium carboxanilide turnover ($IC_{50}$), compared with untreated control cultures was calculated.

Transient Transfection and Luciferase Reporter Gene Assay $5 \times 10^6$ L428 cells in 1 ml medium were transiently transfected by means of electroporation with 10 µg NF-κB-luc, IkBaM and CMV-GFP. Cells were seeded into six-well plates with additional 2 ml of plain medium. After 24 h incubation at 37° C., GFP transfected cells were examined for green flourescence as indicator of transfection efficacy, which varied from 5% to 10%. Cells were incubated either with 20 µg/ml 5F11+100 µg/ml GaH for 2 h, or with 10 ng/ml bortezomib or both or plain media for 12 h at 37° C. After harvesting the cells were washed twice in PBS (phosphate buffered saline).

Lysis was performed using 1 ml ice-cold reporter lysis buffer (Promega), and lysates were frozen at −70° C. for 1 hour. Luciferase activity was measured using 30 µl lysate in a 96-well luminometry-plate and analyzed by luminometry. Untreated cells, transfected with the reporter gene were used to obtain baseline NF-κB-activity. All assays were done in triplicate to obtain means and standard deviations.

TUNEL Assay and Detection of NF-κB with Indirect Immunofluorescence

Cytospins were provided (1 min at 1000 U/min) to determine the effect of 5F11 and/or bortezomib on apoptosis and NFκB-activation in L428 and L540 cells on the single cell level. $2 \times 10^5$ cells were seeded in six-well microtiter plates in 3 ml plain media (control) or with 5F11+GaH (5 µg/25 µg per ml) or bortezomib (10 nM) or both. Incubation time was 30 min for 5F11, 1 h for crosslinking GaH and at least six hours for bortezomib, all at 37° C. The slides were dried overnight at room temperature and fixed using ice-cold acteone (30 sec incubation). The TUNEL assay was performed using the In Situ Cell Death Detection Kit, TMR red (Roche) according to the manufacturers instructions. Finally, cells were mounted with VECTASHIELD Mounting Medium containing DAPI (Vector Laboratories, Burlingame, Calif.) or stained with an rabbit-anti-p65 antibody (Santa Cruz, 10 nM) and a second FITC-labeled mouse-anti-rabbit antibody (10 nM). Cytospin preparations were analyzed by fluorescence microscopy.

In order to exclude non-specific antibody binding, slides of untreated cells were stained either with rabbit-anti-p65-IgG, or FITC-conjugated mouse-anti-rabbit-IgG, or DAPI.

Annexin V Binding Assay $2 \times 10^5$ L540 cells were incubated (in triplicate) either with 5F11/GaH, bortezomib, or both, or in plain medium as described above at 37° C. for 12 h. To detect apoptotic cells, the translocation of phosphatidylserine to the outer leaflet of the plasma membrane was determined by flow cytometry (FACS calibur Bengton & Dickinson Flow Cytometer) after staining with annexin V conjugated to fluorescein as recommended (Annexin V-FITC apoptosis detection kit I, BD Bioscience, USA). Triplicateswere used to calculate means and standard deviations.

SDS-PAGE and Western Blotting

Whole cell protein extracts were prepared in 1× Laemmli solution (10 µg) were separated using sodium dodecyl sulfate polyacrylamide gel electrophoresis (SDS-PAGE) using 4-15% gels. Proteins were transferred to a nitrocellulose membrane (Hybond-C, Amersham Pharmacia Biotech Inc., Freiburg, Germany) and blocked with Roti-Block (Roth, Karlsruhe, Germany) for 1 h at room temperature. Immunoblots were incubated with the primary antibodies obtained from the Apoptosis Sampler Kits I and II (BD Bioscience, CA) in PBS with 10% fetal calf serum as recommended. The c-flip specific antibody was purchased from Sigma (F-6550). Bound antibodies were detected with horseradish peroxidase-conjugated secondary donkey-anti-mouse or rabbit-IgG mAb (Dianova, Hamburg, Germany) or horseradish peroxidaseconjugated goat-anti-mouse IgG (Dianova) diluted 1/10000. The proteins were visualized using the ECL Western blotting detection reagents (Amersham Pharmacia) according to manufacturers instructions.

Electrophoretic Mobility Shift Assay

Electrophoretic mobility shift assays (EMSA) were performed to visualize binding of NF-κB to DNA. Nuclear protein extract (5 µg; 20 mM HEPES, pH 7.9, 400 mM NaCl, 1 mM EDTA, 1 mM EGTA) from cells treated with different antibodies were incubated with $^{32}$P-labeled oligonucleotides with the NF-κB binding sequence (Santa Cruz) for 30 minutes at room temperature. The DNA/protein complexes were separated using electrophoresis on 6% native polyacrylamide gels.

Xenograft Model of Human HD

The xenograft model of human HD has been described previously (17). Subcutaneous solid L540Cy tumors were established by injection of L540Cy cells ($1 \times 10^7$) resuspended in 200 µL PBS into the right flank of pathogen-free severe combined immunodeficiency (SCID) mice (FOX CHASE SCID; Taconic M&B A/S, Ry, Denmark). Tumor development was measured every 3 days and the tumor volume was determined using the formula (length×width×height/2). Animals with established tumors of about 100 mm$^3$ were divided randomly into four groups, which received 100 µg 5F11 (in 200 µL PBS intraperitoneally) and 6 hours later 10 ng bortezomib i.v. by tail vein or each agent alone for a total of 4 injections. Control mice received PBS only. The experiment was stopped and the mice killed when the median tumor diameter in the control group exceeded 2500 mm$^3$ (day 50). The treatment and control groups consisted of 4 animals each and results were confirmed by repeating the experiments.

Results

The Combination of 5F11 Antibody and Bortezomib Increases the Cytotoxicity Against HD- and ALCL-Derived Cell Lines The cellular reponse to 5F11 in the partial apoptosis-resistent HD-derived cell line L540 on the single cell level was analyzed. To visualize binding of 5F11 and apoptosis simultaneously, L540 cells were incubated with 5F11 and a FITC labeled crosslinking goat-anti human antibody before performing a TUNEL assay. All L540 cells were stained after incubation with 5F11 and GaH-FITC indicating that the whole population was positive for CD30. A TUNEL assay with these cells revealed that all cells bound 5F11 at a comparable level, but only a subset of the cells were rendered apoptotic. These data suggest that the differential response of L540 cells to CD30 stimulation via 5F11 might be due to heterogenous expression of downstream signalling molecules even in a single cell type. One such candidate known to be expressed in Hodgkin cells is the transcription factor NF-κB, which protects tumor cells from apoptosis.

If 5F11 induces NF-κB activation in L540 cells, and thus rendering the cells resistance to apoptosis, then the apoptosis rate should be enhanced upon inhibition of NF-κB. Therefore cells were exposed to MG132, a proteasome inhibitor known to inhibit the degradation of the NF-κB repressor IkB, in combination with 5F11/GaH. The combination of 5F11 and MG132 induced apoptosis in most of the cells, although subtoxic concentrations of each of the agents were used. The rate of apoptosis was quantified by means of annexin-V staining and FACS analysis. The antibody or MG132 alone did not enhance apoptosis compared to the control, while the apoptosis rate of the combination was approximately 60%. Taken together, the data demonstrate a synergistic effect of 5F11-mediated-CD30 crosslinking and bortezomib on the induction of apoptosis (see Fig. M-1G).

Figure 2:
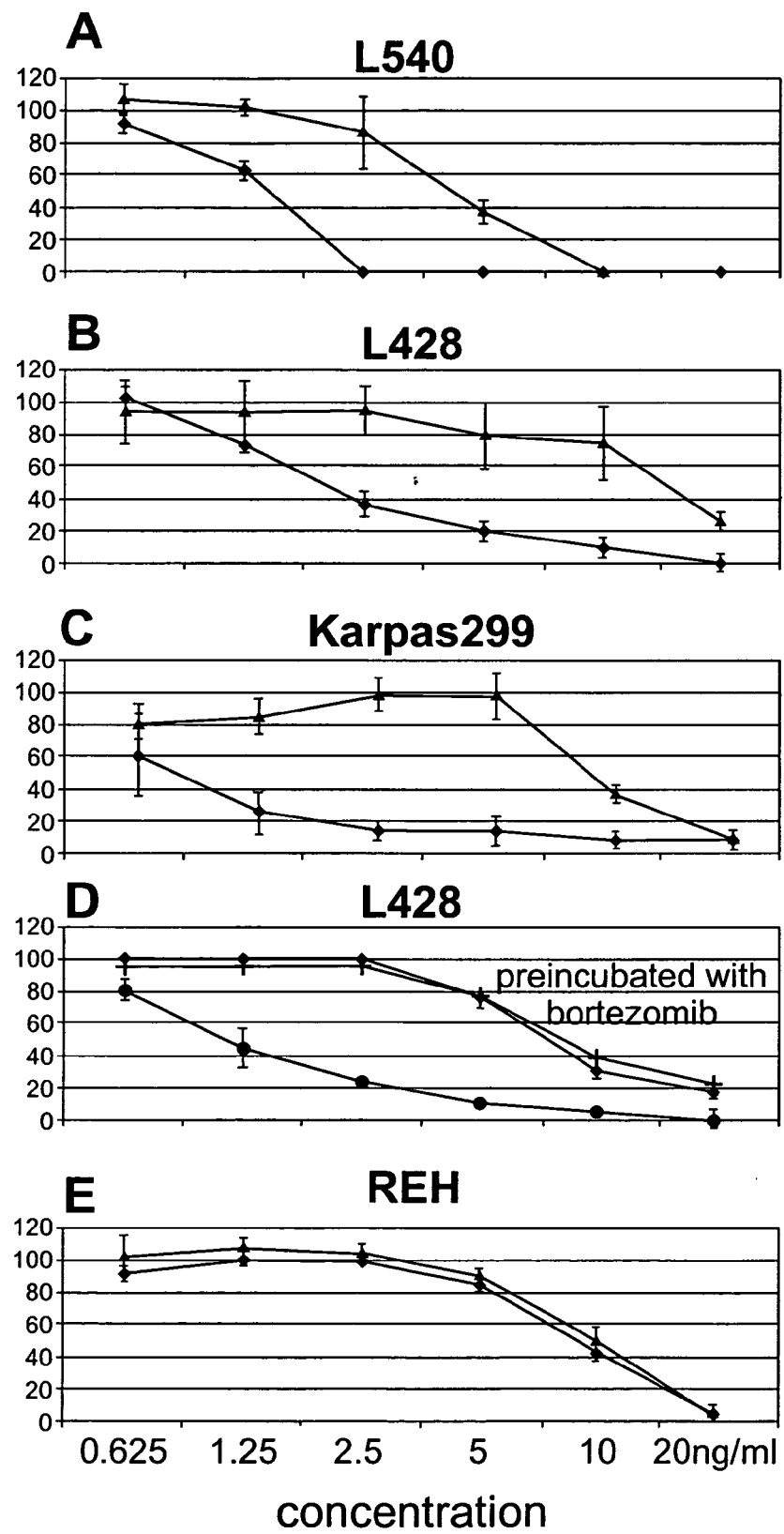
FIG. 2: The combination of crosslinked 5F11 and MG132 decreases the cell viability of CD30 expressing cell lines An XTT-assay showing viability of the Hodgkin cell lines L540 (A), L428 (B) and the ALCL line Karpas299 (C) and the CD30 negative cell line REH (E) after exposure to increasing amounts of bortezomib in the presence (diamond) or absence (triangle) of 5F11. Subtoxic concentrations of 5F11 and the crosslinking GaH antibody were combined with increasing concentrations of bortezomib. The cells were pre-incubated with the mabs for 30 minutes before bortezomib was added. The cell viability was estimated after 48 hours of incubation. The $IC_{50}$ of bortezomib is decreased in the presence of 5F11 for the CD30-expressing cells. Pre-incubation of the cells with bortezomib for 30 minutes before addition of 5F11 does not increase the cytoxicity of bortezomib for L428 cells (D). The results of control experiments (5F11 diamond) and goat-anti-human antibody (cross) and 5F11+GaH (circle) are indicated. The figure is representative for three independent experiments.

The cytotoxic potential of 5F11 and proteasome inhibition was determined by XTT viability assays on different cell lines. Shown are experiments that utilized the proteasome inhibitor bortexomib, however similar results were obtained using MG132 (data not shown). In each of the cell lines tested the combination of bortezomib with 5F11 clearly decreased cell viability. At a concentration of bortezomib (25 ng/ml) that resulted in minimal reduction of viability, L540 cells were completely killed when pre-treated with subtoxic concentrations of 5F11. Similar results were obtained for Karpas 299 cells and for L428 cells, which are resistant to 5F11 even at higher concentrations (17). To analyze if 5F11 pre-incubation is required for the synergy, the sequence was changed by incubating L428 first with bortezomib for 30 minutes followed by incubation with the antibody. As shown in FIG. 2 this setting did not enhance the cytotoxic activity of bortezomib. Thus, CD30 signaling induced by 5F11 binding may be important for the dramatic increase of the cytotoxity of bortezomib against HD-derived cell lines.

To prove whether the cytotoxic synergy is specific for CD30, XTT assays were performed with the acute lymphocytic leukemia cell line REH, which does not express CD30. REH cells were also killed by bortezomib in a dose dependent manner, whereas pre-incubation with 5F11 had no effect on its cytotoxic potential (FIG. 2E).

Figure 3:
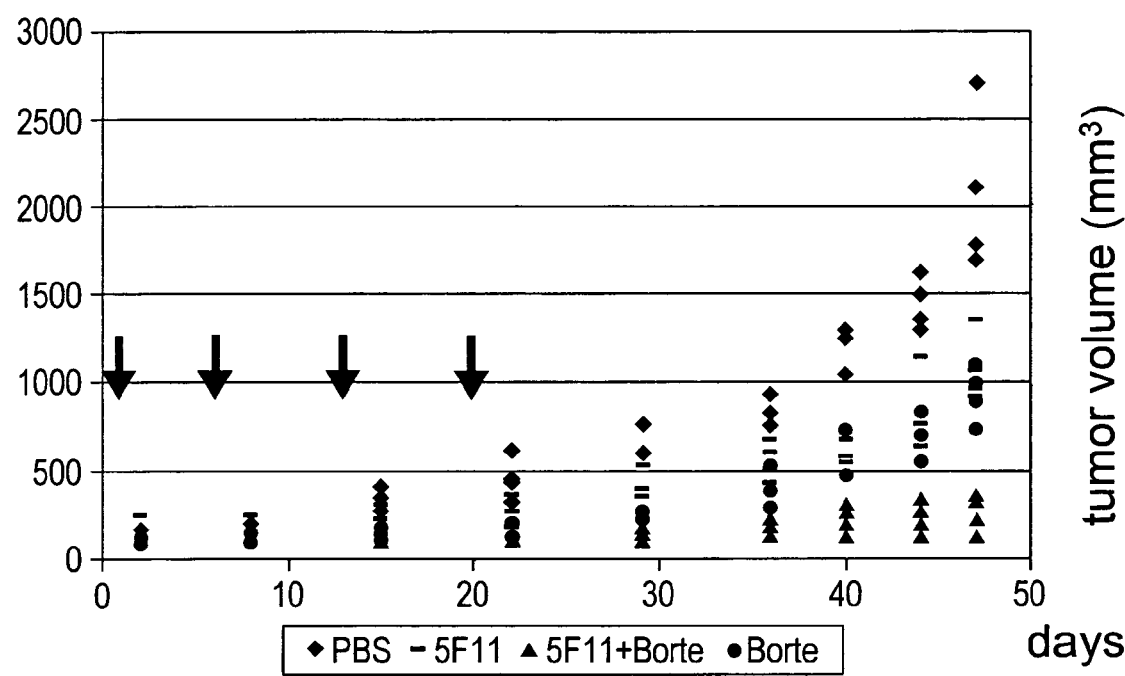
FIG. 3: Effect of 5F11 and bortezomib on the tumor growth of subcutaneous L540Cy Hodgkin tumors in SCID mice. The mice were randomly divided into four groups when the L540 derived tumors reached a volume of about 100 mm3 to receive PBS, 5F11 (100 µg), bortezomib (10 ng) or the combination of 5F11 and bortezomib. The tumor volume of each mouse is given. The arrows indicate the days of treatment. In an independent experiment, these results were reproduced with 4 animals in the 5F11 and the 5F11+bortezomib group, respectively (data not shown).

In Vivo Activity of the Combination of 5F11 and Bortezomib in a Human Hodgkin Model The activity of the bortezomib and 5F11 combination was also analyzed in a solid subcutaneous L540Cy Hodgkin tumor model. Tumor bearing mice were administered either 5F11, bortezomib, the combination of 5F11 and bortezomib or PBS. The animals were first injected with 5F11 and bortezomib was then administered 6 hours later; treatment was repeated once for 4 days (q×days×4). As shown in FIG. 3, both 5F11 and bortezomib induced significantly delayed tumor growth compared to the control group receiving PBS. Even more promising results were obtained in animals treated with a combination of 5F11 and bortezomib, as the tumor growth was almost completely inhibited. Most importantly the growth inhibition was maintained for several weeks after treatment (indicated with arrows), whereas the tumors of the animals receiving either 5F11 or bortezomib alone showed tumor progression. Sections of tumors derived from L540 tumor bearing mice treated as indicated were stained with hematoxyline. The density of tumor cells within the tissue was dramatically decreased after treatment with 5F11 in combination with bortezomib. The histological examination of L540 tumors 6 weeks after treatment shows tumor free areas within the tumor tissue derived from mice treated with the combination of 5F11 and bortezomib.

5F11 Dependent CD30 Signaling Activates NF-κB

F-κB subunit p65 was detected using an anti-p65 mab and a secondary FITClabeled antibody on methanol fixed untreated L540 cell. The expression level and nuclear localisation of NF-κB is increased after stimulation with crosslinked 5F11, whereas exposure to bortezomib leads to an exclusion of NF-κB from the cell nuclei (cell nuclei were stained with DAPI).

The data suggest that 5F11 alone may not be sufficient to induce apoptosis in all Hodgkin cell lines and the resistant population seems to exhibit an enhanced sensitivity against bortezomib. Such an effect might be due to the activation of the survival factor NF-κB, a key factor of apoptosis resistance in HD. In addition, NF-κB is one of the best characterised targets for bortezomib. The subcellular distribution of NF-κB in the Hodgkin cell lines L540 and L428 was analyzed after incubation with crosslinked 5F11 and/or bortezomib. A low level expression of the NF-κB subunit p65 was detectable in untreated L540 cells. The protein was localized in the cytoplasm and partly in the cell nuclei, reflecting a constitutive expression of NF-κB in Hodgkin cells (4). Incubation with 5F11/GaH induced an increase of NF-κB dependent antibody staining and a nuclear accumulation, demonstrating NF-κB activation in response to CD30 signaling. This effect was inhibited when bortezomib was given 30 minutes after 5F11 stimulation and lead to the exclusion of NF-κB from the cell nucleus, which was observed after 6 and 8 hours. The comparison with the NF-κB staining of untreated cells indicates that even the constitutively expressed NF-κB is sequestered in the cytoplasm. Similar results were obtained with L428 cells analyzing the NF-κB distribution after treatment with 5F11±bortezomib.

Figure 4:
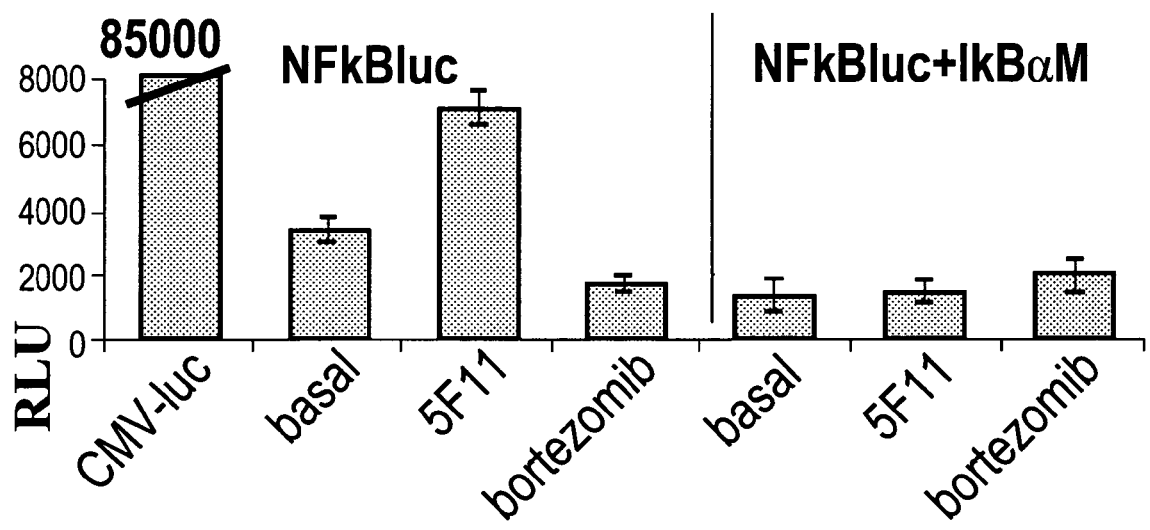
FIG. 4: Effect of 5F11 and bortezomib on the subcellular distribution and transcriptional activity of NF-κB L428 cells were transfected with either the reporter constructs pCMV-luc (transfection control) or pNF-κB-luc (bar 2-4) or pNF-κB-luc together with the expression vector IkBM (bar 5-7). The transfection efficacy was about 10% and the total amount of DNA was kept constant. After an over night recovery period transfectants were treated with PBS (basal), 5F11 or bortezomib for 24 hours. The luciferase activity (RLU) of the cells were measured and is given to indicate the relative levels of NF-κB-dependent promoter activity.

L428 cells transfected with a NF-κB-responsive luciferase reporter gene were used to measure the activation of the transcriptional activity of NF-κB (FIG. 4. The stimulation with 5F11 resulted in about two-fold activation of the reporter gene. This activation was supressed in the presence of bortezomib, which also reduced the basal activity of the NF-κB reporter. No activation of the luciferase gene was seen when an expression vector encoding IkBaM, the constitutive active mutant of the NF-κB inhibitor IkB, was co-transfected, indicating that the effects measured are NF-κB specific. The DNA-binding activity of NF-κB in cells after exposure to 5F11 was determined using an electrophoretic mobility shift assay (EMSA). NF-κB DNA binding was detectable in untreated L540 as well as in L428 cells and exposure to crosslinked 5F11 enhanced DNA binding in both cell lines. The anti-CD30 antibody Ber-H2 used as a control failed to activate NF-κB in this setting (lane 3 and 6) and did not induce any increase of the sensitivity of HD-derived cell lines to bortezomib as measured in XTT assays. In support of this notion, it was found that the vital cells of 5F11-treated L540 cells revealed a strong NF-κB staining not seen in the apoptotic cells.

The Expression Level of the Anti-Apoptotic Protein C-Flip is Modulated by 5F11 and Bortezomib Several factors hae been reported to block the apoptotic cascade, and therefore the expression level of candidate proteins related to NF-κB activation of pro-survival genes was measured by Western blotting. Interestingly most dramatic changes were seen for the expression of the caspase inhibitor c-flip. c-flip is induced strongly in L540 and L428 cells after CD30 stimulation with 5F11. In contrast, a downregulation of c-flip was seen after co-incubation of the cells with bortezomib for 6, 8 and 16 hours. Only minor changes in bcl-2 and bax expression were observed and the expression levels of TRADD and FADD remained unaltered following 5F11 crosslinking or bortezomib treatment.

Discussion

The present Example provides evidence that resistance to CD30-mediated cell death in HD cells is due to an activation of NF-κB which can be overcome by treatment with the proteasome inhibitor bortezomib. This conclusion was made from: (1) analyzing the effects of CD30 stimulation through the human antibody 5F11 on NF-κB expression at the single cell level, where an increased expression in the apoptosis of resistant cells was observed. This was seen in the L428 cell line that is insensitive to 5F11-mediated cell death and also in the resistant population of the partly sensitive cell line L540; and (2) the inhibition of NF-κB using subtoxic concentrations of bortezomib in the presence of 5F11 caused a sharp increase in apoptosis. This was shown in vitro and in a subcutaneous HD tumor model, since a combination of 5F11 and bortezomib inhibited tumor growth more efficiently than each agent alone. The advantage of the combination over 5F11 treatment alone was most prominent after two to three weeks, reflecting the kinetics of the 5F11-mediated signaling. Initial stimulation with 5F11 induced apoptosis in some cells, whereas the resistent cells showed a proliferation rate comparable and even higher than estimated for untreated control cells. Although the CD30 receptor has been used for targeted immunotherapy in various studies, the clinical evaluation for many monoclonal antibodies and antibody-toxin conjugates has been disappointing (18-21). One example is the unconjugated mAb Ber-H2, which is capable of killing malignant cells effectively in vitro, but revealed no therapeutic benefit clinically (20). Very similar, an immunotoxin of Ber-H2 conjugated to saporin toxin showed only transient responses in HD patients (21). The data presented here suggest that a combination of CD30 directed immunotherapy with bortezomib will improve the clinical results.

TNF-R1 is a receptor of the TNF family capable of triggering apoptosis via the recruitment of adapter proteins, but can also protect cells from death due to activation of NF-κB and anti-apoptotic target genes (recent review: (22)). In transfected HeLa cells the TNF-RI-induced cell death can be enhanced by costimulation with TNF-R2, CD40 or CD30. This seems to depend on the depletion of TRAF2 (23), one of the TNF-R associating factors crucial for NF-κB activation. The CD30 mediated depletion of co-transfected TRAF-2, NF-κB deactivation and enhanced apoptosis is also seen in a transfected embryonic nephrocarcinoma cell line (24, 25) and the ALCL line Karpas299 (15). However this mechanism has so far not been shown in HD-derived cells and recently for TRAF1 a differential function in HD lymphoma and ALCL derived cells has been reported (26). In contrast, the instant Example demonstrated that a direct inhibition of the NF-κB pathway using bortezomib clearly enhances the CD30 mediated apoptosis rate in HD- and in ALCL-derived cell lines.

The sensitization of initially resistant tumor cells to TRAIL mediated apoptosis with bortezomib does not primarily depend on NF-κB inhibition, as an enhanced cleavage of caspase8 (27) and the reduction of the antiapoptotic protein c-flip, respectively (28) seems to overcome resistance. We observed that expression of c-flip which is upregulated by NF-κB and also subject to ubiquitination and proteasomal degradation (29, 30) is activated after stimulation of CD30 but decreases when bortezomib is added. Interestingly c-flip has recently been shown to be the key regulator of death receptor resistance in H-RS cells (31-33). Expression of c-flip in HD cells is also dependent on aberrantly active MEK/ERK pathway regulated by CD30, CD40 and RANK signaling (34).

NF-κB reporter gene assays, immunofluorescence and Western blotting demonstrated that 5F11 stimulation leads to an initial activation of NF-κB and downstream anti-apoptotic protein c-flip, suggesting that CD30 signalling via 5F11 induces sensitization of the tumor cells to bortezomib. It can be concluded that the balance of apoptosis induction and growth stimulation in response to CD30 signaling is shifted to apoptosis when CD30 stimulation is combined with proteasome inhibition; The in vitro and in vivo activity of the combination of 5F11 and bortezomib seen in the present Example suggests a therapeutic value for the treatment of HD patients.

ADDITIONAL REFERENCES

1. Croft, M. Costimulation of T cells by OX40, 4-1BB, and CD27. Cytokine Growth Factor Rev, 14: 265-273, 2003.
2. Cheng, X., Kinosaki, M., Murali, R., and Greene, M. I. The TNF receptor superfamily: role in immune inflammation and bone formation. Immunol Res, 27: 287-294, 2003.
3. Izban, K. F., Ergin, M., Huang, Q., Qin, J. Z., Martinez, R. L., Schnitzer, B., Ni, H., Nickoloff, B. J., and Alkan, S. Characterization of NF-kappaB expression in Hodgkin's disease: inhibition of constitutively expressed NF-kappaB results in spontaneous caspase-independent apoptosis in Hodgkin and Reed-Sternberg cells. Mod Pathol, 14: 297-310, 2001.
4. Horie, R., Higashihara, M., and Watanabe, T. Hodgkin's lymphoma and CD30 signal transduction. Int J Hematol, 77: 37-47, 2003.
5. Horie, R., Watanabe, T., Morishita, Y., Ito, K., Ishida, T., Kanegae, Y., Saito, I., Higashihara, M., Mori, S., and Kadin, M. E. Ligand-independent signaling by overexpressed CD30 drives NF-kappaB activation in Hodgkin-Reed-Sternberg cells. Oncogene, 21: 2493-2503, 2002.
6. Schneider, C. and Hubinger, G. Pleiotropic signal transduction mediated by human CD30: a member of the tumor necrosis factor receptor (TNFR) family. Leuk Lymphoma, 43: 1355-1366, 2002.
7. Smith, C. A., Farrah, T., and Goodwin, R. G. The TNF receptor superfamily of cellular and viral proteins: activation, costimulation, and death. Cell, 76: 959962, 1994.
8. Arch, R. H., Gedrich, R. W., and Thompson, C. B. Tumor necrosis factor receptor-associated factors (TRAFs)—a family of adapter proteins that regulates life and death. Genes Dev, 12: 2821-2830, 1998.
9. Baker, S. J. and Reddy, E. P. Modulation of life and death by the TNF receptor superfamily. Oncogene, 17: 3261-3270, 1998.
10. Chiarle, R., Podda, A., Prolla, G., Podack, E. R., Thorbecke, G. J., and Inghirami, G. CD30 overexpression enhances negative selection in the thymus and mediates programmed cell death via a Bcl-2-sensitive pathway. J Immunol, 163: 194-205, 1999.
11. Su, C. C., Chiu, H. H., Chang, C. C., Chen, J. C., and Hsu, S. M. CD30 is involved in inhibition of T-cell proliferation by Hodgkin's Reed-Sternberg cells. Cancer Res, 64: 2148-2152, 2004.
12. Tarkowski, M. Expression and a role of CD30 in regulation of T-cell activity. Curr Opin Hematol, 10: 267-271, 2003.

13. Chakrabarty, S., Nagata, M., Yasuda, H., Wen, L., Nakayama, M., Chowdhury, S. A., Yamada, K., Jin, Z., Kotani, R., Moriyama, H., Shimozato, O., Yagita, H., and Yokono, K. Critical roles of CD30/CD30L interactions in murine autoimmune diabetes. Clin Exp Immunol, 133: 318-325, 2003.

14. Gruss, H. J., Boiani, N., Williams, D. E., Armitage, R. J., Smith, C. A., and Goodwin, R. G. Pleiotropic effects of the CD30 ligand on CD30-expressing cells and lymphoma cell lines. Blood, 83: 2045-2056, 1994.

15. Mir, S. S., Richter, B. W., and Duckett, C. S. Differential effects of CD30 activation in anaplastic large cell lymphoma and Hodgkin disease cells. Blood, 96: 4307-4312, 2000.

16. Levi, E., Pfeifer, W. M., and Kadin, M. E. CD30-activation-mediated growth inhibition of anaplastic large-cell lymphoma cell lines: apoptosis or cell-cycle arrest? Blood, 98: 1630-1632, 2001.

17. Borchmann, P., Treml, J. F., Hansen, H., Gottstein, C., Schnell, R., Staak, O., Zhang, H. F., Davis, T., Keler, T., Diehl, V., Graziano, R. F., and Engert, A. The human anti-CD30 antibody 5F11 shows in vitro and in vivo activity against malignant lymphoma. Blood, 102: 3737-3742, 2003.

18. Horie, R. and Watanabe, T. The biological basis of Hodgkin's lymphoma. Drug News Perspect, 16: 649-656, 2003.

19. Barth, S., Huhn, M., Matthey, B., Tawadros, S., Schnell, R., Schinkothe, T., Diehl, V., and Engert, A. Ki-4(scFv)-ETA', a new recombinant anti-CD30 immunotoxin with highly specific cytotoxic activity against disseminated Hodgkin tumors in SCID mice. Blood, 95: 3909-3914, 2000.

20. Falini, B., Flenghi, L., Fedeli, L., Broe, M. K., Bonino, C., Stein, H., Durkop, H., Bigema, B., Barbabietola, G., Venturi, S., and et al. In vivo targeting of Hodgkin and Reed-Sternberg cells of Hodgkin's disease with monoclonal antibody Ber-H2 (CD30): immunohistological evidence. Br J Haematol, 82: 3845, 1992.

21. Falini, B., Bolognesi, A., Flenghi, L., Tazzari, P. L., Broe, M. K., Stein, H., Durkop, H., Aversa, F., Comeli, P., Pizzolo, G., and et al. Response of refractory Hodgkin's disease to monoclonal anti-CD30 immunotoxin. Lancet, 339: 1195-1196, 1992.

22. Wajant, H., Henkler, F., and Scheurich, P. The TNF-receptor-associated factor family: scaffold molecules for cytokine receptors, kinases and their regulators. Cell Signal, 13: 389-400, 2001.

23. Fotin-Mleczek, M., Henkler, F., Samel, D., Reichwein, M., Hausser, A., Panmryd, I., Scheurich, P., Schmid, J. A., and Wajant, H. Apoptotic crosstalk of TNF receptors: TNF-R2-induces depletion of TRAF2 and IAP proteins and accelerates TNF-R1-dependent activation of caspase-8. J Cell Sci, 115: 27572770, 2002.

24. Duckett, C. S., Gedrich, R. W., Gilfillan, M. C., and Thompson, C. B. Induction of nuclear factor kappaB by the CD30 receptor is mediated by TRAF1 and TRAF2. Mol Cell Biol, 17: 1535-1542, 1997.

25. Duckett, C. S. and Thompson, C. B. CD30-dependent degradation of TRAF2: implications for negative regulation of TRAF signaling and the control of cell survival. Genes Dev, 11: 2810-2821, 1997.

26. Durkop, H., Hirsch, B., Hahn, C., Foss, H. D., and Stein, H. Differential expression and function of A20 and TRAF1 in Hodgkin lymphoma and anaplastic large cell lymphoma and their induction by CD30 stimulation. J Pathol, 200: 229-239, 2003.

27. Johnson, T. R., Stone, K., Nikrad, M., Yeh, T., Zong, W. X., Thompson, C. B., Nesterov, A., and Kraft, A. S. The proteasome inhibitor PS-341 overcomes TRAIL resistance in Bax and caspase 9-negative or Bcl-xL overexpressing cells. Oncogene, 22: 4953-4963, 2003.

28. Sayers, T. J., Brooks, A. D., Koh, C. Y., Ma, W., Seki, N., Raziuddin, A., Blazar, B. R., Zhang, X., Elliott, P. J., and Murphy, W. J. The proteasome inhibitor PS-341 sensitizes neoplastic cells to TRAIL-mediated apoptosis by reducing levels of c-FLIP. Blood, 102: 303-310, 2003.

29. Kreuz, S., Siegmund, D., Scheurich, P., and Wajant, H. NF-kappaB inducers upregulate cFLIP, a cycloheximide-sensitive inhibitor of death receptor signaling. Mol Cell Biol, 21: 3964-3973, 2001.

30. Kim, K. W., Kim, B. J., Chung, C. W., Jo, D. G., Kim, I. K., Song, Y. H., Kwon, Y. K., Woo, H. N., and Jung, Y. K. Caspase cleavage product lacking aminoterminus of IkappaBalpha sensitizes resistant cells to TNF-alpha and TRAILinduced apoptosis. J Cell Biochem, 85: 334-345, 2002.

31. Mathas, S., Lietz, A., Anagnostopoulos, I., Hummel, F., Wiesner, B., Janz, M., Jundt, F., Hirsch, B., Johrens-Leder, K., Vornlocher, H. P., Bommert, K., Stein, H., and Dorken, B. c-FLIP Mediates Resistance of Hodgkin/Reed-Sternberg Cells to Death Receptor-induced Apoptosis. J Exp Med, 199: 1041-1052, 2004.

32. Thomas, R. K., Kallenborn, A., Wickenhauser, C., Schultze, J. L., Draube, A., Vockerodt, M., Re, D., Diehl, V., and Wolf, J. Constitutive expression of c-FLIP in Hodgkin and Reed-Sternberg cells. Am J Pathol, 160: 1521-1528, 2002.

33. Dutton, A., ONeil, J. D., Milner, A. E., Reynolds, G. M., Starczynski, J., Crocker, J., Young, L. S., and Murray, P. G. Expression of the cellular FLICEinhibitory protein (c-FLIP) protects Hodgkin's lymphoma cells from autonomous Fas-mediated death. Proc Natl Acad Sci USA, 101: 6611-6616, 2004.

34. Zheng, B., Fiumara, P., Li, Y. V., Georgakis, G., Snell, V., Younes, M., Vauthey, J. N., Carbone, A., and Younes, A. MEK/ERK pathway is aberrantly active in Hodgkin disease: a signaling pathway shared by CD30, CD40, and RANK that regulates cell proliferation and survival. Blood, 102: 1019-1027, 2003.

EQUIVALENTS

Those skilled in the art will recognize, or be able to ascertain using no more than routine experimentation, many equivalents of the specific embodiments of the invention described herein. Such equivalents are intended to be encompassed by the following claims.

INCORPORATION BY REFERENCE

All patents, pending patent applications and other publications cited herein are hereby incorporated by reference in their entirety.

We claim:

1. A method of treating Hodgkin's disease (HD) in a subject, comprising administering (a) a monoclonal antibody that binds CD30 and (b) a proteasome inhibitor to the subject, wherein the antibody induces CD30 signaling, activates NF-κB, and increases expression of the caspase inhibitor, c-flip, in the HD-derived cells.

2. A method of treating Hodgkin's disease (HD) in a subject, comprising (a) selecting a monoclonal antibody that binds CD30, induces CD30 signaling, activates NF-KB, and increases expression of the caspase inhibitor, c-flip, in the HD-derived cells and (b) administering the antibody and a proteasome inhibitor to the subject.

3. The method of claim 1, wherein the proteasome inhibitor inhibits chymotrypsin-like activity of the 26S proteasome.

4. The method of claim 1, wherein the proteasome inhibitor is selected from bortezomib, ALLnL (N-acetyl-leucinyl-leucynil-norleucynal, MG101), LLM (N-acetyl-leucinyl-leucynil-methional), Z-LLnV (carbobenzoxyl-leucinyl-leucynil-norvalinal,MG115), Z-LLL (carbobenzoxyl-leucinyl-leucynil-leucynal, MG132), Lactacystine, b-lactone, Boronic Acid Peptides, Ubiquitin Ligase Inhibitors, Cyclosporin A, FK506 (Tacrolimus) and Deoxyspergualin.

5. The method of claim 1 wherein the proteasome inhibitor is bortezomib.

6. The method of claim 1, wherein the antibody comprises a human IgG heavy chain and a human kappa light chain.

7. The method of claim 1, wherein the antibody comprises a human IgG1 or IgG3 heavy chain.

8. The method of claim 1, wherein the antibody binds to human CD30 with an affinity constant of at least $10^8$ $M^{-1}$.

9. The method of claim 1, wherein the antibody binds to human CD30 with an affinity constant of at least $10^9$ $M^{-1}$.

10. The method of claim 1, wherein the antibody is human, chimeric, or humanized.

11. The method of claim 1, wherein the antibody is non-fucosylated.

12. The method of claim 1 wherein the antibody comprises heavy chain and light chain variable regions comprising the amino acid sequences shown in SEQ ID NO:2 and SEQ ID NO:4, respectively, or an antibody which competes for binding to CD30 with an antibody comprising heavy chain and light chain variable regions comprising the amino acid sequences shown in SEQ ID NO:2 and SEQ ID NO:4, respectively.

13. The method of claim 1 wherein the antibody comprises a heavy chain and a light chain variable regions comprising the amino acid sequences shown in SEQ ID NO: 6 and SEQ ID NO:8, respectively, or an antibody which competes for binding to CD30 with an antibody comprising heavy chain and light chain variable regions comprising the amino acid sequences shown in SEQ ID NO:6 and SEQ ID NO:4, respectively.

14. The method of claim 1, wherein the antibody comprises a heavy chain and a light chain variable regions comprising the amino acid sequences shown in SEQ ID NO: 10 and SEQ ID NO:12, respectively, or an antibody which competes for binding to CD30 with an antibody comprising heavy chain and light chain variable regions comprising the amino acid sequences shown in SEQ ID NO:10 and SEQ ID NO:12, respectively.

15. The method of claim 1, where the antibody is produced by a hybridoma, wherein the hybridoma is prepared from a B cell obtained from a transgenic non-human animal having a genome comprising a human heavy chain transgene or transchromosome and a human light chain transgene or transchromosome, fused to an immortalized cell.

16. The method of claim 1, wherein the antibody is administered prior to, or simultaneous with, administration of the proteasome inhibitor.

* * * * *